US009192719B2

(12) United States Patent
Rogers et al.

(10) Patent No.: US 9,192,719 B2
(45) Date of Patent: Nov. 24, 2015

(54) IMPLANTABLE MEDICAL PUMP DIAGNOSTICS

(75) Inventors: Charles R. Rogers, Maple Grove, MN (US); Irfan Z. Ali, Woodbury, MN (US); Ronald L. Mezera, Lake Elmo, MN (US); Keith A. Miesel, St. Paul, MN (US); Scott A. Sarkinen, Greenfield, MN (US); Nicholas R. Whitehead, Hopkins, MN (US)

(73) Assignee: Medtronic, Inc., Minneapolis, MN (US)

( * ) Notice: Subject to any disclaimer, the term of this patent is extended or adjusted under 35 U.S.C. 154(b) by 404 days.

(21) Appl. No.: 12/916,720

(22) Filed: Nov. 1, 2010

(65) Prior Publication Data
US 2012/0109099 A1 May 3, 2012

(51) Int. Cl.
A61M 5/168 (2006.01)
A61M 5/142 (2006.01)

(52) U.S. Cl.
CPC ....... *A61M 5/16809* (2013.01); *A61M 5/14216* (2013.01); *A61M 5/14276* (2013.01); *A61M 2005/16863* (2013.01); *A61M 2005/16868* (2013.01); *A61M 2005/16872* (2013.01)

(58) Field of Classification Search
CPC ......... A61M 2005/16863; A61M 2005/16872; A61M 2005/16868; A61B 5/7246; A61B 5/721; A61B 2562/221; A61B 2562/22; A61B 2562/227
USPC ......... 604/65–67, 890.1, 891.1, 151; 73/1.02; 417/413.1–413.2
See application file for complete search history.

(56) References Cited

U.S. PATENT DOCUMENTS

| 3,727,463 | A | * | 4/1973 | Intraub ............................ 73/702 |
| 4,624,661 | A | * | 11/1986 | Arimond ...................... 604/151 |
| 4,692,145 | A | | 9/1987 | Weyant |
| 4,715,852 | A | | 12/1987 | Reinicke et al. |
| 4,985,015 | A | | 1/1991 | Obermann et al. |
| 5,020,362 | A | * | 6/1991 | Hart et al. ................... 73/114.43 |
| 5,342,176 | A | * | 8/1994 | Redlich ......................... 417/212 |
| 5,387,909 | A | * | 2/1995 | Neel et al. ..................... 340/931 |
| 5,390,105 | A | * | 2/1995 | Worley et al. ................... 700/79 |
| 5,502,365 | A | * | 3/1996 | Nanbu et al. .................. 318/798 |
| 6,031,707 | A | * | 2/2000 | Meyer ............................ 361/153 |

(Continued)

FOREIGN PATENT DOCUMENTS

| AU | 525126 B2 | 10/1982 |
| EP | 1338295 A1 | 8/2003 |

(Continued)

OTHER PUBLICATIONS

Dorf (Chapter 2. Voltage and Current Sources. The Electrical Engineering Handbook, Second Edition. Edited by Richard C. Dorf, CRC Press 2000).*

(Continued)

*Primary Examiner* — Aarti B Berdichevsky
*Assistant Examiner* — Matthew A Engel
(74) *Attorney, Agent, or Firm* — Shumaker & Sieffert, P.A.

(57) ABSTRACT

A method of detecting a fault condition within an implantable medical pump comprises delivering therapeutic fluid using a medical pump comprising an actuation mechanism configured to be energized to provide a pump stroke, detecting a property associated with energizing the actuation mechanism, and determining whether the property associated with energizing the actuation mechanism indicates that a fault condition exists with the medical pump.

54 Claims, 13 Drawing Sheets

(56) References Cited

U.S. PATENT DOCUMENTS

| | | | |
|---|---|---|---|
| 6,260,004 B1* | 7/2001 | Hays et al. ................... 702/183 |
| 6,454,377 B1* | 9/2002 | Ishizaki ........................ 347/15 |
| 6,555,986 B2* | 4/2003 | Moberg ........................ 318/685 |
| 6,595,756 B2* | 7/2003 | Gray et al. ................... 417/44.1 |
| 6,615,114 B1* | 9/2003 | Skiba et al. .................. 700/275 |
| 6,757,665 B1* | 6/2004 | Unsworth et al. ............. 706/15 |
| 6,827,702 B2 | 12/2004 | Lebel et al. |
| 6,941,785 B2 | 9/2005 | Haynes et al. |
| 6,945,760 B2 | 9/2005 | Gray et al. |
| 7,022,116 B2 | 4/2006 | Morris |
| 7,054,782 B2 | 5/2006 | Hartlaub |
| 7,056,890 B2* | 6/2006 | Najarian ........................ 514/23 |
| 7,099,852 B2* | 8/2006 | Unsworth et al. ............. 706/23 |
| 7,151,963 B2* | 12/2006 | Havel et al. ................... 607/5 |
| 7,290,993 B2* | 11/2007 | Vogeley et al. ............. 417/413.2 |
| 7,367,968 B2 | 5/2008 | Rosenberg et al. |
| 7,553,818 B2* | 6/2009 | Najarian ........................ 514/23 |
| 7,569,030 B2 | 8/2009 | Lebel et al. |
| 7,581,434 B1* | 9/2009 | Discenzo et al. ............. 73/53.01 |
| 7,621,893 B2 | 11/2009 | Moberg et al. |
| 7,659,256 B2* | 2/2010 | Najarian ........................ 514/23 |
| 7,674,776 B2* | 3/2010 | Najarian ........................ 514/23 |
| 7,776,029 B2* | 8/2010 | Whitehurst et al. ....... 604/890.1 |
| 7,922,462 B2* | 4/2011 | Preuthun et al. ............ 417/413.1 |
| 8,007,247 B2* | 8/2011 | Sarkinen et al. ............ 417/44.11 |
| 8,167,168 B2* | 5/2012 | Reynolds ........................ 222/1 |
| 8,246,573 B2* | 8/2012 | Ali et al. ........................ 604/65 |
| 8,353,619 B2* | 1/2013 | Lauharn et al. ............ 366/127 |
| 2002/0016568 A1 | 2/2002 | Lebel et al. |
| 2002/0058906 A1 | 5/2002 | Lebel et al. |
| 2002/0087114 A1 | 7/2002 | Hartlaub |
| 2002/0198513 A1 | 12/2002 | Lebel et al. |
| 2004/0260233 A1* | 12/2004 | Garibotto et al. .............. 604/66 |
| 2006/0293849 A1 | 12/2006 | Baldwin |
| 2007/0112301 A1* | 5/2007 | Preuthun et al. .............. 604/151 |
| 2007/0270782 A1 | 11/2007 | Miesel et al. |
| 2008/0132290 A1 | 6/2008 | Sharabi et al. |
| 2008/0294098 A1* | 11/2008 | Sarkinen et al. ................. 604/67 |
| 2008/0306359 A1* | 12/2008 | Zdeblick et al. ................. 600/302 |
| 2009/0062667 A1 | 3/2009 | Fayram et al. |
| 2009/0082757 A1 | 3/2009 | Rogers et al. |
| 2009/0090186 A1* | 4/2009 | Linzenkirchner et al. ...... 73/587 |
| 2009/0099506 A1 | 4/2009 | Estes et al. |
| 2009/0131769 A1* | 5/2009 | Leach et al. ................... 600/309 |
| 2010/0176754 A1* | 7/2010 | Navarra et al. ..................... 318/8 |
| 2010/0300702 A1* | 12/2010 | Andrews et al. ............... 166/373 |
| 2011/0262535 A1* | 10/2011 | Najarian et al. ............... 424/458 |
| 2011/0264006 A1* | 10/2011 | Ali et al. ........................ 600/587 |
| 2011/0319881 A1* | 12/2011 | Johnston ......................... 606/33 |
| 2012/0109099 A1* | 5/2012 | Rogers et al. ................... 604/500 |
| 2012/0196881 A1* | 8/2012 | Najarian et al. ............... 514/269 |

FOREIGN PATENT DOCUMENTS

| | | |
|---|---|---|
| WO | 03023226 A1 | 3/2003 |
| WO | 03089034 A1 | 10/2003 |
| WO | 2010026570 A2 | 3/2010 |
| WO | 2011136862 A1 | 11/2011 |

OTHER PUBLICATIONS

Notification of Transmittal of the International Search Report and the Written Opinion for corresponding patent application No. PCT/US2011/049878, mailed Dec. 27 2011, 10 pages.

U.S. Appl. No. 12/768,336, filed Apr. 27, 2010, Ali et al.

* cited by examiner

IMPLANTABLE MEDICAL PUMP DIAGNOSTICS

TECHNICAL FIELD

The present disclosure relates to medical devices and, more particularly implantable fluid delivery devices.

BACKGROUND

Implantable fluid delivery devices are used to treat a number of physiological, psychological, and emotional conditions, including chronic pain, tremor, Parkinson's disease, epilepsy, urinary or fecal incontinence, sexual dysfunction, obesity, spasticity, or gastroparesis. For some medical conditions, an implantable fluid delivery device provides the best, and in some cases the only, therapy to restore a patient to a more healthful condition.

An implantable fluid delivery device typically provides a patient with a programmable dosage or infusion of a drug or other therapeutic agent. The fluid delivery device typically includes a reservoir for storing the therapeutic agent, a fill port, a pumping mechanism to pump the therapeutic agent from the reservoir, a catheter to transport the therapeutic agent from the reservoir to a patient's anatomy, and electronics to control the pumping mechanism.

SUMMARY

In general, the disclosure relates to systems and methods for delivering a therapeutic fluid to a patient using an implantable medical pump and to systems and methods for determining when a fault condition exists within the medical pump.

In one example, the disclosure is directed to a method of detecting a fault condition within an implantable medical pump, the method comprising delivering therapeutic fluid using a medical pump comprising an actuation mechanism configured to be energized to provide a pump stroke, detecting a property associated with energizing the actuation mechanism, and determining whether the property associated with energizing the actuation mechanism indicates that a fault condition exists with the medical pump.

In another example, the disclosure is directed to a medical device system comprising a medical pump configured to deliver a therapeutic fluid to a patient, the medical pump comprising an actuation mechanism configured to be energized to provide a pump stroke, a sensor configured to detect a property associated with energizing the actuation mechanism, and a processor configured to determine whether the property associated with energizing the actuation mechanism indicates that a fault condition exists with the medical pump In another example, the disclosure is directed to a medical device system comprising means for delivering a therapeutic fluid to a patient, the means for delivering the therapeutic fluid comprising means for actuating the fluid and to provide a pump stroke, means for detecting a property associated with energizing the means for actuating the fluid, and means for determining whether the property associated with the energizing the actuating the fluid indicates that a fault condition with the means for actuating the fluid exists.

In another example, the disclosure is directed to a computer-readable medium containing instructions. The instructions cause a programmable processor to direct the delivery of a therapeutic fluid using a medical pump comprising an actuation mechanism configured to be energized to provide a pump stroke, detect a property associated with energizing the actuation mechanism, and determine whether the property associated with energizing the actuation mechanism indicates that a fault condition exists within the medical pump.

The details of one or more examples of the invention are set forth in the accompanying drawings and the description below. Other features, objects, and advantages of the invention will be apparent from the description and drawings, and from the claims.

DETAILED DESCRIPTION

An implantable fluid delivery device may include a pump, such as an electromagnetic piston pump, for delivering a fluid, such as a drug or other therapeutic agent, for delivery to a patient. In some cases, the pump may experience a fault condition, such as a stalled pump motor, a partially stalled pump motor, or an air locked motor, that render the pump partially or totally inoperable. In general, this disclosure is directed to techniques for providing an implantable fluid delivery device with the ability to detect and identify fault conditions so that the fluid delivery device will become aware that the medical pump is malfunctioning.

In one example, a method may include delivering therapeutic fluid using a medical pump comprising an actuation mechanism configured to be energized to provide a pump stroke, detecting a property associated with energizing the actuation mechanism, and determining that the property associated with energizing the actuation mechanism indicates that a fault condition exists with the medical pump. In one example, the method may also include initiating a recovery action to attempt to resolve a fault condition that is detected within the medical pump. The method may also include initiating an alarm if and when a fault condition is detected and/or if and when a recovery action fails to resolve the fault condition.

This disclosure is also generally directed, in some examples, to a system including a medical device that may include a medical pump configured to deliver a therapeutic fluid to a patient, the medical pump comprising an actuation mechanism configured to be energized to provide a pump stroke, a sensor configured to detect a property associated with energizing the actuation mechanism, and a processor configured to determine when the property associated with energizing the actuation mechanism indicates that a fault condition exists with the medical pump.

Figure 1:
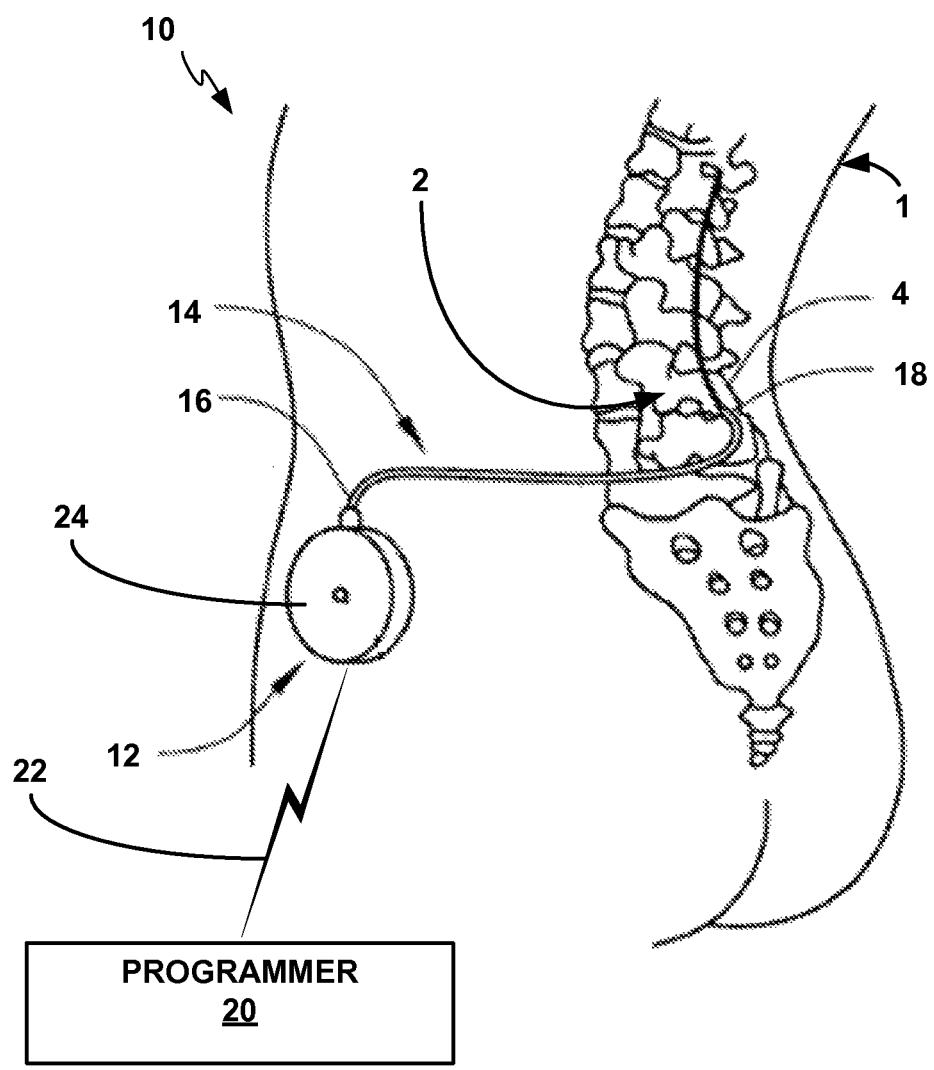
FIG. 1 is a conceptual diagram illustrating an example of a fluid delivery system, which includes an implantable fluid delivery device with a medical pump that is configured to deliver a therapeutic agent to a patient via a catheter.

FIG. 1 is a schematic diagram of an example system 10, including an implantable medical device (IMD) 12, which is configured to deliver a therapeutic agent, such as a pharmaceutical agent, for example a drug, insulin, pain relieving agent, anti-inflammatory agent, gene therapy agent, or the like, to a target site 2 within a patient 1. The therapeutic agent is delivered via a catheter 14 that is coupled to IMD 12. Catheter 14 may comprise a plurality of catheter segments, or catheter 14 may be a unitary catheter. In the example shown in FIG. 1, target site 2 is proximate to spinal cord 4 of patient 1.

A proximal end 16 of catheter 14 is coupled to IMD 12 while a distal end 18 of catheter 14 is positioned proximate target site 2. System 10 may also include an external programmer 20 that communicates with IMD 12 as needed, such as to provide or retrieve therapy information or therapy parameters associated with therapy delivery. For example, external programmer 20 may be configured to turn IMD 12 on or off, to deliver the initial therapy parameters for patient 1, to modify the therapy parameters, and so forth. In one example, external programmer 20 communicates with IMD 12 wirelessly 22, as shown in FIG. 1.

Although patient 1 is generally referred to as a human patient in the present disclosure, system 10 can be used with other mammalian or non-mammalian patients. IMD 12 may be employed to treat, manage or otherwise control various conditions or disorders of patient 1, including, e.g., pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders.

IMD 12 may be configured to deliver one or more therapeutic agents, alone or in combination with other therapies, including, e.g., electrical stimulation. For example, in some cases, a medical pump may deliver one or more pain-relieving drugs to patients with chronic pain, insulin to a patient with diabetes, or other fluids to patients with different disorders. IMD 12 may be implanted in patient 1 for chronic or temporary therapy delivery.

IMD 12 includes an outer housing 24 that is constructed of a biocompatible material that resists corrosion and degradation from bodily fluids, such as titanium or biologically inert polymers. IMD 12 may be implanted within a subcutaneous pocket close to target site 2. For example, as shown in FIG. 1, IMD 12 may be implanted within the abdomen of patient 1 close to the position along spinal cord 4 where target site 2 is located. In other examples, IMD 12 may be implanted within other suitable sites within patient 1, which may depend, for example, on where target site 2 is located within patient 1, and the ease of implanting IMD 12 within suitable locations near target site 2.

Catheter 14 may be coupled to IMD 12 either directly or with the aid of a catheter extension (not shown). In the example shown in FIG. 1, catheter 14 traverses from the implant site of IMD 12 to target site 2 proximate to spinal cord 4. Catheter 14 is positioned such that one or more fluid delivery outlets of catheter 14 are proximate to one or more locations within patient 1. In the example shown in FIG. 1, IMD 12 delivers a therapeutic agent to one or more locations at target site 2 within patient 1. IMD 12 delivers a therapeutic agent to target site 2 proximate spinal cord 4 with the aid of catheter 14. For example, IMD 12 may be configured for intrathecal drug delivery into the intrathecal space or epidural space surrounding spinal cord 4.

In some examples, multiple catheters may be coupled to IMD 12 to target the same or different tissue or nerve sites within patient 1. Thus, although a single catheter 14 is shown in FIG. 1, in other examples, system 10 may include multiple catheters or catheter 14 may define multiple lumens for delivering different therapeutic agents to patient 1 or for delivering a therapeutic agent to different tissue sites within patient 1. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein with reference to the example of FIG. 1.

IMD 12 may deliver one or more therapeutic agents to patient 1 according to one or more therapy programs. Example therapeutic agents that IMD 12 may be configured to deliver include insulin, morphine, hydromorphone, bupivacaine, clonidine, other analgesics, genetic agents, antibiotics, nutritional fluids, analgesics, hormones or hormonal drugs, gene therapy drugs, anticoagulants, cardiovascular medications or chemotherapeutics. A therapy program, generally speaking, may set forth different therapy parameters, such as a therapy schedule specifying programmed doses, dose rates for the programmed doses, and specific times to deliver the programmed doses.

The therapy programs may be a part of a program group for therapy, wherein the group includes a plurality of constituent therapy programs and/or therapy schedules. In some examples, IMD 12 may be configured to deliver a therapeutic agent to patient 1 according to different therapy programs on a selective basis. IMD 12 may include a memory to store one or more therapy programs, instructions defining the extent to which patient 1 may adjust therapy parameters, switch between therapy programs, or undertake other therapy adjustments. Patient 1 may select and/or generate additional therapy programs for use by IMD 12 via external programmer 20 at any time during therapy or as designated by the clinician.

In one example, programmer 20 is an external computing device that is configured to communicate with IMD 12, such as via a wireless communications link 22. For example, programmer 20 may be a clinician programmer that the clinician uses to communicate with IMD 12. Alternatively, programmer 20 may be a patient programmer that allows patient 1 to view and modify therapy parameters. A clinician programmer may include additional or alternative programming features, relative to a patient programmer, which may have more limited features such as limited programming capability. For example, more complex or sensitive tasks may only be allowed by the clinician programmer to prevent patient 1 from making undesired changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured to an application to simulate programmer 20. Alternatively, a notebook computer, tablet computer, or other personal computer may execute an application to function as programmer 20, e.g., with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 14, the position of catheter 14 within patient 1, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

A clinician uses programmer 20 to program IMD 12 with one or more therapy programs that define the therapy delivered by IMD 12. During a programming session, the clinician may determine one or more therapy programs, which may include one or more therapy schedules, programmed doses, dose rates of the programmed doses, and specific times to deliver the programmed doses that may provide effective therapy to patient 1. Patient 1 may provide feedback to the clinician as to the efficacy of a specific therapy program being evaluated or desired modifications to the therapy program. Once the clinician has identified one or more programs that may be beneficial to patient 1, patient 1 may continue the evaluation process and determine which dosing program or therapy schedule best alleviates the condition of patient 1 or otherwise provides efficacious therapy to patient 1.

In some cases, programmer 20 may be configured for use by patient 1. When configured as a patient programmer, programmer 20 may have limited functionality in order to prevent patient 1 from altering critical functions or applications that may be detrimental to patient 1. In this manner, programmer 20 may only allow patient 1 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 1 when therapy is being delivered or when IMD 12 needs to be refilled or when the power source within programmer 20 or IMD 12 needs to be replaced or recharged.

Whether programmer 20 is configured for clinician or patient use, programmer 20 may communicate to IMD 12 or any other computing device via wireless communication. Programmer 20, for example, may communicate via wireless communication link 22 with IMD 12 using any of a number of radio frequency (RF) telemetry techniques. Programmer 20 may also communicate with another programmer or computing device via a wired or wireless connection using any of a variety of local wireless communication techniques, such as RF communication according to one or more specification sets, such as the Medical Implant Communication Service (MICS) specification set, Medical Implant Telemetry System (MITS), Medical Data Service (MEDS), 802.11, or Bluetooth specification sets, infrared (IR) communication according to the IRDA specification set, or other standard or proprietary telemetry protocols. Programmer 20 may also communicate with another programmer or computing device via exchange of removable media, such as magnetic or optical disks, or memory cards or sticks. Further, programmer 20 may communicate with IMD 12 and another programmer via remote telemetry techniques, communicating via a local area network (LAN), wide area network (WAN), public switched telephone network (PSTN), or cellular telephone network, for example.

Figure 2:
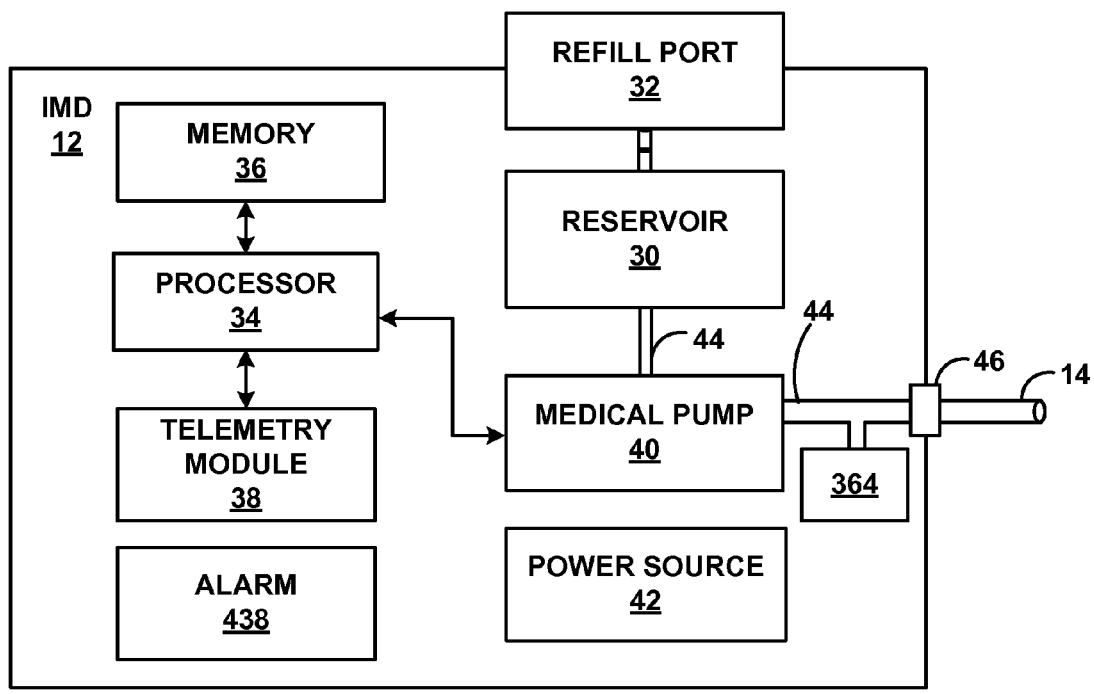
FIG. 2 is functional block diagram illustrating an example fluid delivery device with a medical pump.

FIG. 2 is a functional block diagram illustrating components of an example IMD 12. The example IMD 12 shown in FIG. 2 includes reservoir 30, refill port 32, processor 34, memory 36, telemetry module 38, medical pump 40, power source 42, internal channels 44, catheter 14, and catheter access port (CAP) 46. IMD 12 may also include sensors that are used to determine the status of medical pump 40 or other components within IMD 12, such as a pressure sensor 364 used to measure the pressure at the outlet of medical pump 40 (described in more detail below).

Refill port 32 provides for refilling of reservoir 30 with therapeutic fluid. Refill port 32 may comprise a self-sealing injection port. The self-sealing injection port may include a self-sealing membrane to prevent loss of therapeutic agent delivered to reservoir 30 via refill port 32. After a delivery system, e.g., a hypodermic needle, penetrates the membrane of refill port 32, the membrane may seal shut when the delivery system is removed from refill port 32. Internal channels 44 may comprise one or more segments of tubing and/or a series of cavities that run from reservoir 30, around or through medical pump 40 to catheter access port 46.

Processor 34 controls the operation of medical pump 40 with the aid of software instructions associated with program information that is stored in memory 36. In one example, processor 34 is configured to run the software instructions in order to control operation of IMD 12. For example, the software instructions may define therapy programs that specify the amount of a therapeutic agent that is delivered to a target tissue site within patient 1 from reservoir 30 via catheter 14, e.g., dose, the rate at which the agent is delivered, e.g., dosage rate, and the time at which the agent will be delivered and the time interval over which the agent will be delivered, e.g., the therapy schedule for dose or doses defined by program. In other examples, a quantity of the therapeutic agent may be delivered, at least in part, according to one or more physiological characteristics of a patient, e.g., physiological characteristics sensed by one or more sensors (not shown) implanted within a patient as part of therapy system 10 (FIG. 1), or according to a combination of scheduled doses and physiological characteristics. In some examples, a patient may be permitted to increase or reduce one or more doses.

Processor 34 can include one or more processors, including one or more microprocessors, digital signal processors (DSPs), application specific integrated circuits (ASICs), field programmable gate arrays (FPGAs), or any other equivalent integrated or discrete logic circuitry, as well as any suitable combination of such components. The term "processor" or "processing circuitry" may generally refer to any of the foregoing logic circuitry, alone or in combination with other logic circuitry, or any other equivalent circuitry.

Memory 36 may include any volatile or non-volatile media, such as a random access memory (RAM), read only memory (ROM), non-volatile RAM (NVRAM), electrically erasable programmable ROM (EEPROM), flash memory, and the like. As mentioned above, memory 36 may store program information including instructions for execution by processor 34, such as, but not limited to, therapy programs, historical therapy programs, timing programs for delivery of the therapeutic agent from reservoir 30 to catheter 14, and any other information regarding therapy of patient 1. Memory 36 may include separate memory portions for storing instructions, patient information, therapy parameters (e.g., grouped into sets referred to as "dosing programs"), therapy adjustment information, program histories, and other categories of information such as any other data that may benefit from separate physical memory modules.

Telemetry module 38 in IMD 12, as well as telemetry modules in programmers, such as external programmer 20, may accomplish communication by RF communication techniques. In addition, telemetry module 38 may communicate with programmer 20 via proximal inductive interaction of IMD 12 with external programmer 20. Processor 34 controls telemetry module 38 to send and receive information.

Power source 42 delivers operating power to various components of IMD 12. Power source 42 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, non-rechargeable storage devices may be used for a limited period of time. As a further alternative, an external inductive power supply could transcutaneously power IMD 12 whenever measurements are needed or desired.

Medical pump 40 may be a mechanism that delivers a therapeutic agent in some metered or other desired flow dosage to target site 2 within patient 1 from reservoir 30 via catheter 14. Medical pump 40 may include an actuation mechanism that is electrically energized to provide a pump stroke to move fluid from reservoir 30. The actuation mechanism may comprise an electromagnetic coil and an actuator that is movable in response to electrical energization of the coil. Other actuation mechanisms may be used, such as a piezoactuator.

Figure 3:
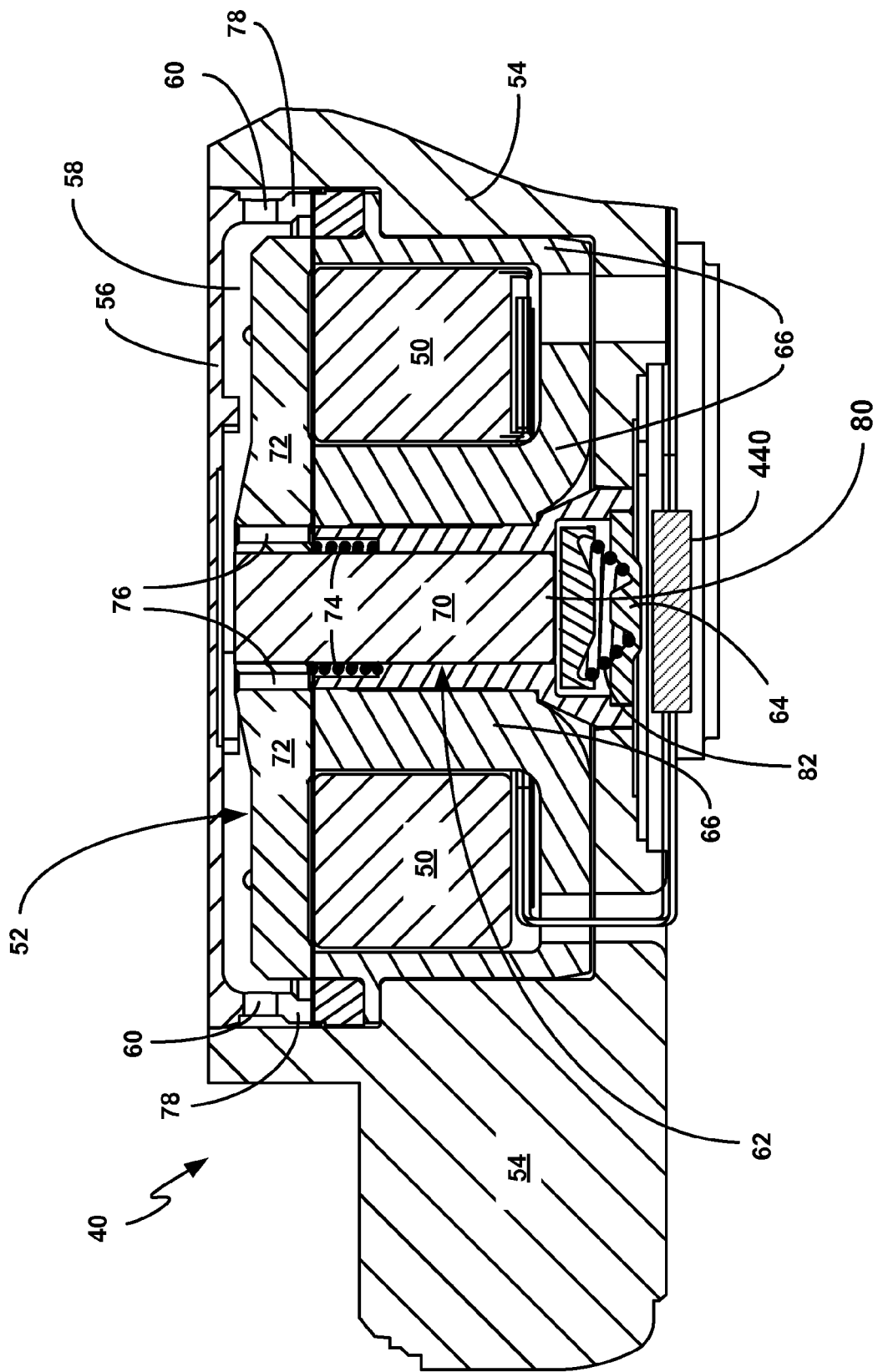
FIG. 3 is a broken section view of an example medical pump for use in the fluid delivery device of FIG. 1.

FIG. 3 is a broken section view of an example of medical pump 40 including electromagnetic coil 50, actuator 52, bulkhead 54, and cover 56. During the operation of medical pump 40, the therapeutic agent flows from reservoir 30 into chamber 58 formed within bulkhead 54. In one example, the therapeutic agent enters chamber 58 through holes 60 in cover 56. Once within chamber 58, the therapeutic agent enters central aperture 62 and is pushed by the motion of actuator 52 through one-way valve 64. After passing through one-way valve 64, the therapeutic agent is directed through internal channels 44 to catheter 14 and onto to one or more target sites within the patient. For example, as shown in FIG. 1, catheter 14 may be used to direct the therapeutic agent from medical pump 40 to target site 2 within patient 1.

Electromagnetic coil 50 comprises one or more insulated conductors arranged in a multitude of turns. As examples, electromagnetic coil 50 may include a single continuous conductor or more than one conductor electrically connected in series or in parallel. Current is delivered to electromagnetic coil 50 to produce a magnetic field that moves actuator 52 through a pump stroke from a rearward position (upward in FIG. 3) to a forward position (downward in FIG. 3). In one example, electromagnetic coil 50 is retained in a magnetic cup 66 that includes a highly magnetic material that efficiently magnetizes in response to current through electromagnetic coil 50. As an example, magnetic cup 66 may include a highly magnetic steel alloy, such as a highly magnetic stainless steel alloy such as, for example, 430F stainless steel.

In the example shown in FIG. 3, actuator 52 includes a piston 70 and an armature 72. Actuator 52 is positioned such that piston 70 is located within central aperture 62. A spring 74 is located within central aperture 62 adjacent armature 72. Spring 74 biases actuator 52 into a rearward position away from coil 50 (upward as shown in FIG. 3). Armature 72 is made from a magnetic material, such as a stainless steel. When coil 50 and magnetic cup 66 are magnetized, armature 72 is attracted to and moves toward magnetic cup 66 so that actuator 52 moves to a forward position (downward as shown in FIG. 3), producing a pump stroke. The therapeutic agent flows into chamber 58 where it is forced out of medical pump 40 by the motion of actuator 52. In one example, the therapeutic agent flows through holes 60 formed in cover 56 into chamber 58, through holes 76 in armature 72 and/or around armature 72 through a gap between armature 72 and a sidewall 78 of cover 56 and into central aperture 62, where the therapeutic agent is forced out one-way valve 64 by piston 70 when actuator 52 is driven from the rearward position to the forward position. Because armature 72 is within the therapeutic agent flow path, the material of armature 72 should resist corrosion, such as a magnetic stainless steel alloy that is corrosion resistant, such as AL29-4 stainless steel.

Piston 70 may be interference fit to armature 72 or secured to armature 72 by other suitable techniques. Like armature 72, piston 70 is located within the therapeutic agent flow path and should resist corrosion. In one example, piston 70 comprise a sapphire material, which resists corrosion and limits wear between piston 70 and central aperture 62 caused by the pumping action of medical pump 40. Piston 70 may comprise other materials, however, such as a metal material, for example a stainless steel or titanium alloy. In some examples, actuator 52 may comprise a unitary component wherein piston 70 and armature 72 comprise a single magnetic material such as a stainless steel alloy.

Actuator 52 actuates so that armature 72 moves within chamber 58 between the rearward position and the forward position. Spring 74 biases actuator 52 toward the rearward position with armature 72 being pushed against an interior surface of cover 56. Energizing electromagnetic coil 50 magnetizes magnetic cup 66, which in turn attracts armature 72. The magnetic attraction force between armature 72 and magnetic cup 66 overcomes the force of spring 74 to move actuator 52 through a pump stroke from the rearward position to forward position (downward in FIG. 3) to create a pumping action of piston 70. The motion of piston 70 forces the therapeutic agent within central aperture 62 and adjacent to a distal end 80 of piston 70 through one-way valve 64.

Following a pump stroke, current through electromagnetic coil 50 is stopped, and spring 74 biases actuator 52 into its original rearward position with armature 72 pushed against cover 56. As spring 74 moves actuator 52 into the rearward position, the therapeutic agent flows through a small gap between piston 70 and central aperture 62 to fill the growing space within central aperture 62 between distal end 80 of piston 70 and one-way valve 64. While some of the therapeutic agent may flow back though the gap between piston 70 and central aperture 62 during a pump stroke, the speed of piston 70 during a pump stroke combined with the viscosity of the therapeutic agent generally makes any amount of the therapeutic agent flowing back though the gap between piston 70 and the inner surface of central aperture 62 during a pump stroke negligible.

The therapeutic agent pushed by piston 70 during a pump stroke exits medical pump 40 through one-way valve 64. In one example, one-way valve 64 includes a spring 82 that biases one-way valve 64 into a closed position when actuator 52 is not being driven forward. When actuator 52 is driven from the rearward position to the forward position, as described above, the force of the therapeutic agent being pushed forward counteracts the force of spring 82 and opens one-way valve 64 so that the therapeutic agent can flow through one-way valve 64. The configuration of one-way valve 64 may be referred to as a lift check valve. In other examples, different valve configurations may be used including, but not limited to, ball check valves, diaphragm valves, gate valves and other valves. Generally, one-way valve 64 should be selected to minimize a pressure differential in the therapeutic agent flow path at one-way valve 64 while maintaining a fluid seal except during pump strokes.

Further examples of medical pumps that may be used in IMD 12 are disclosed in U.S. Provisional Patent Application Ser. No. 61/174,457, filed on Apr. 30, 2009, the disclosure of which is incorporated herein by reference in its entirety.

Figure 4:
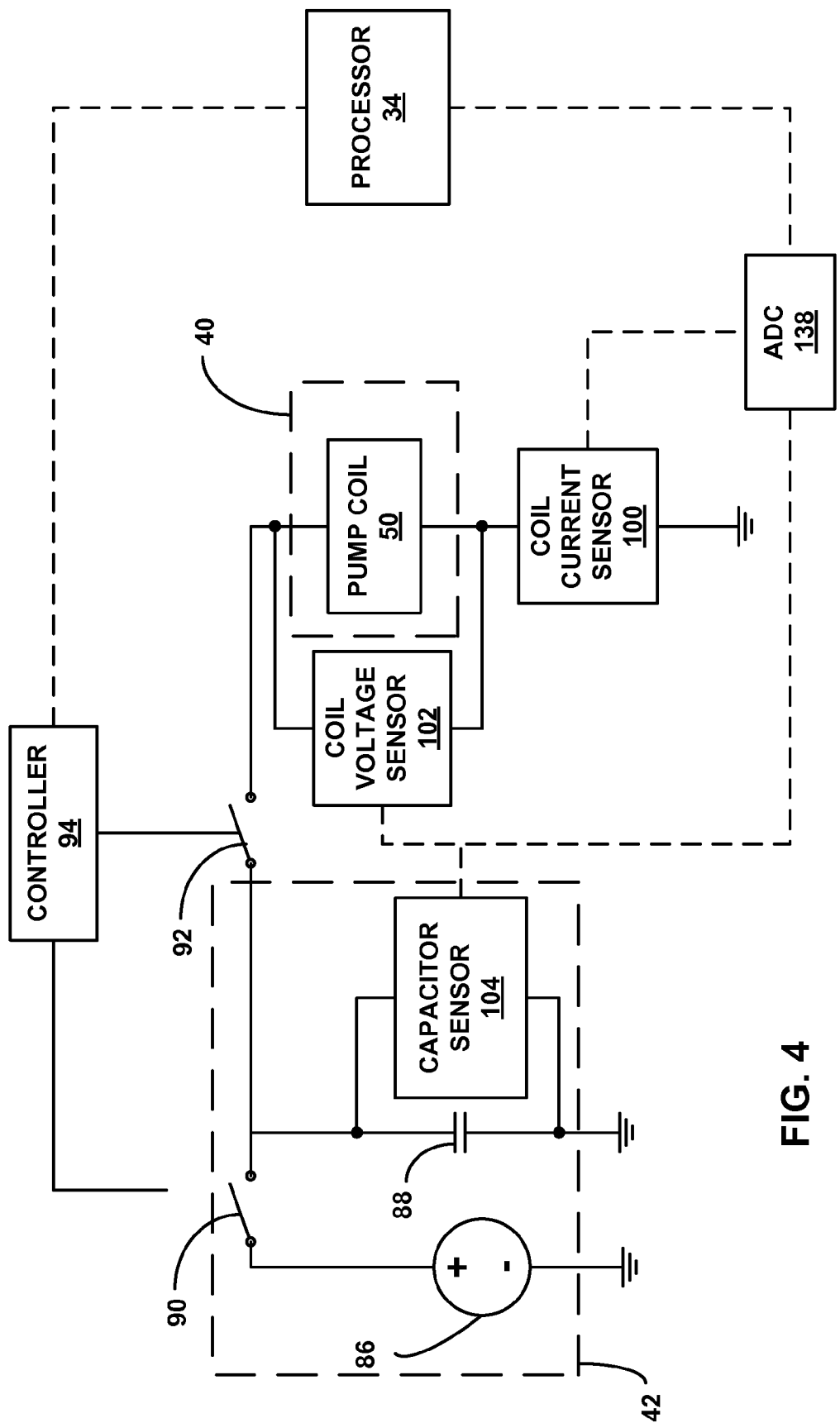
FIG. 4 is a block diagram showing an example circuit for energizing the medical pump and detecting a fault condition.

FIG. 4 is a block diagram of an example circuit for energizing coil 50 and for detecting when a fault condition may exist in medical pump 40. As shown in the example of FIG. 4, power source 42 is electrically connected to medical pump 40. Power source 42 may include a small rechargeable or non-rechargeable battery 86 and a capacitor 88. Although a single capacitor 88 is shown in FIG. 4, power source 42 may comprise a plurality of capacitors connected together, wherein the plurality of capacitors are equivalent to the single capacitor 88 shown in FIG. 4. Battery 86 is operatively connected to capacitor 88 via a first switching device 90 to provide for selective charging of capacitor 88 using battery 86. In one example, capacitor 88 is also operatively connected to coil 50 of medical pump 40 via a second switching device 92 in order to selectively discharge energy from capacitor 88 to coil 50. One or more controllers 94 may be provided to control switching devices 90, 92 for controlling the flow of electrical energy from power source 42 to medical pump 40. In one example, controller 94 receives instructions from processor 34 regarding when medical pump 40 should deliver a pump stroke. FIG. 4 is a schematic block diagram showing an example general setup of a circuit for energizing coil 50. Additional circuitry elements may be included to supplement or enhance the functionality of battery 86, capacitor 88, and switching devices 90, 92.

Use of capacitor 88 provides for a generally fast-response power pulse to coil 50 on command and provides for a reliable constant initial voltage and current across coil 50. When capacitor 88 is charged and processor 34 instructs controller 94 to initiate a pump stroke, controller 94 closes switching device 92 to electrically couple capacitor 88 to coil 50, allowing capacitor 88 to energize coil 50. When coil 50 is energized, a magnetic field is created that drives actuator 52 through a pump stroke, as described above.

Switching device 92 may be opened by controller 94 after a predetermined period of time or after the detection of an end of the pump stroke. Examples of methods of detecting the end of the pump stroke and methods of controlling the pump using end-of-stroke detection is disclosed in pending U.S. patent application Ser. No. 11/805,124, corresponding to U.S. Published Application No. US 2008/0294098, the disclosure of which is incorporated herein by reference in its entirety. Upon the opening of switching device 92, capacitor 88 is electrically decoupled from coil 50, and electrical energy in coil 50 dissipates such that the mechanical force applied by spring 74 (FIG. 3) returns actuator 52 to its rearward position.

After capacitor 88 has been discharged through coil 50 and switching device 92 has been opened, capacitor 88 may be recharged when controller 94 closes switching device 90 between battery 86 and capacitor 88 to electrically couple battery 86 to capacitor 88 in order to recharge capacitor 88 for subsequent pump stroke operation. In this way, capacitor 88 is controlled to charge and discharge to provide the electrical energy to coil 50 as needed to affect a plurality of pump strokes of actuator 52.

It will be recognized by a person of ordinary skill in the art that any suitable switching device capable of providing the switching connections described above may be used for switching device 90 between battery 86 and capacitor 88 and for switching device 92 between capacitor 88 and coil 50 of medical pump 40. For example, switching devices 90, 92 may each be a field-effect transistor (FET) or a junction transistor that is controlled, for example, by controller 94, to close and/or open when commanded. Other suitable electronic or electromagnetic switch configurations, junction transistors, relays, or the like, may be employed as switching devices 90, 92.

Continuing with the block diagram of FIG. 4, IMD 12 may include one or more sensors for detecting a property associated with the energy required to energize coil 50 and drive actuator 52 so that the sensor may be configured to detect whether a particular pump stroke indicates that a fault condition exists in medical pump 40. In one example, IMD 12 includes a current sensor 100 for determining the current passing through coil 50 and/or a voltage sensor 102 for determining the voltage across coil 50. IMD 12 may also include a voltage sensor 104 for determining the voltage across capacitor 88.

Figure 5:
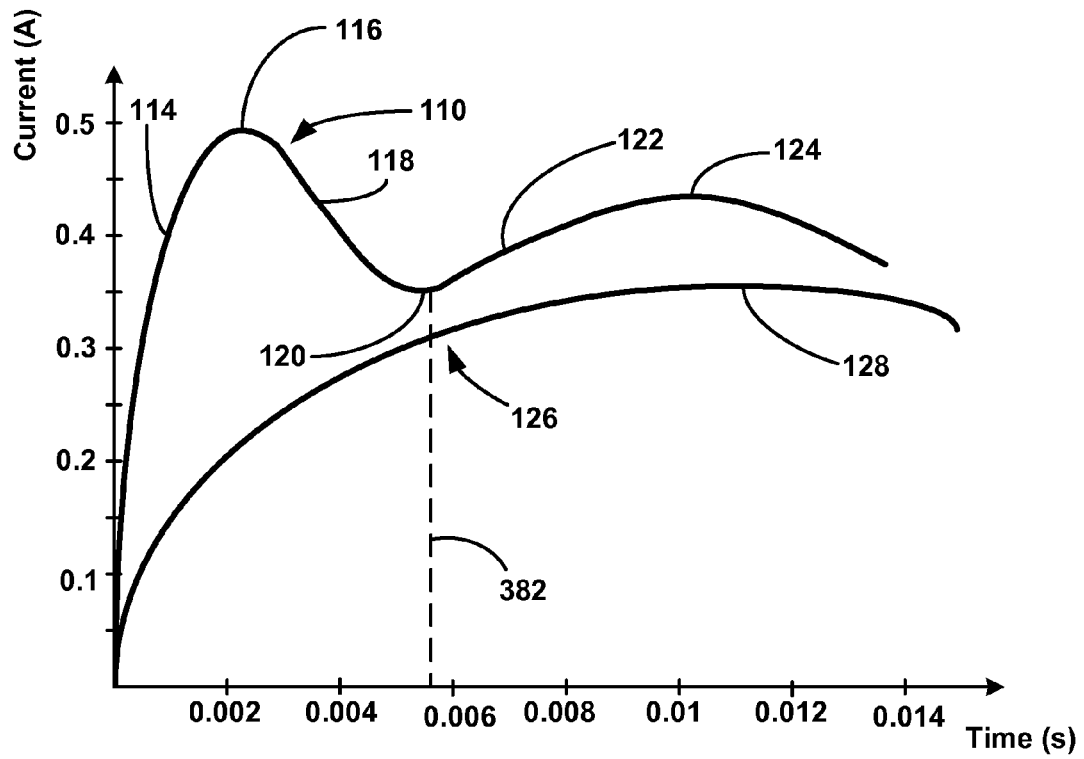
FIG. 5 is a graph showing example current waveforms through a coil of the medical pump for a pump stroke in which no fault condition is present and an attempted pump stroke from a fully-stalled medical pump.

Coil current sensor 100 allows a current waveform of coil 50 to be determined during a pump stroke. Example current waveforms for coil 50 are shown in FIGS. 5-11. FIG. 5 shows an example waveform 110 for medical pump 40 wherein medical pump 40 is operating as expected such that no fault conditions exist. A pump stroke that occurs when no fault condition exists in medical pump 40, e.g., that produces a current waveform similar to waveform 110 shown in FIG. 5, is referred to herein as a "normal" pump stroke of medical pump 40.

As shown in FIG. 5, at time=0, switching device 92 has been closed and current begins to flow from capacitor 88 through coil 50. For an initial segment 114, the current through coil 50 rises quickly up to a maximum current peak 116. At peak 116, actuator 52 begins to move and, as actuator 52 moves, it creates a back electromotive force (EMF) effect that counters the current caused by capacitor 88 such that during a segment 118 the current begins to decline. The back EMF effect continues to cause a decrease in current throughout segment 118 until nadir 120 when actuator 52 completes a pump stroke. The end of the pump stroke results in the inflection point of nadir 120 because the back EMF effect is no longer being produced when actuator 52 is no longer moving. Without the back EMF effect, the current through coil 50 rebounds at segment 122. Throughout this entire time, however, capacitor 88 is depleting its charge such that the voltage provided by capacitor 88, and hence the current that capacitor 88 can provide to coil 50, decays. This decaying of current eventually overtakes the rebound effect in segment 122, and at peak 124 the current begins to decline until capacitor 88 is completely depleted of charge. The actual values of peak 116, trough 120, and final peak 124, as well as the slopes of segments 114, 118, 122, and the segment after final peak 124 may depend on the specific fluid being delivered and the specific configuration of medical pump 40, including the clearance between piston 70 and central aperture 62, the length of a pump stroke, and the pressure necessary to open valve 64.

FIG. 5 also shows an example current waveform 126 for a pump stroke when a fault condition exists in medical pump 40. As described in more detail below, different fault conditions may result in different current waveforms. For example, current waveform 126 shown in FIG. 5 may correspond to a stalled medical pump 40, wherein actuator 52 is not being moved to produce a pump stroke even though current is being delivered to coil 50. The difference in the current waveform between normal pump stroke waveform 110 and a fault-condition waveform, such as stall waveform 126, may be used by processor 34 to determine whether a fault condition exists in medical pump 40. Processor 34 may determine that current waveform 126 corresponds to a stall fault condition because current waveform 126 does not produce an initial peak followed by a nadir, such as peak 116 followed by nadir 120 of normal pump stroke waveform 110. Rather, stall waveform 126 increases in current more slowly than normal waveform 110 to an eventual peak 128. The lack of an inflection point or nadir that would result from an end of stroke is an indicator that actuator 52 did not move at all. In one example, processor 34 may be configured to determine that medical pump 40 has stalled when an attempted pump stroke results in a waveform having no inflection point or nadir indicating an end of stroke.

Figure 6:
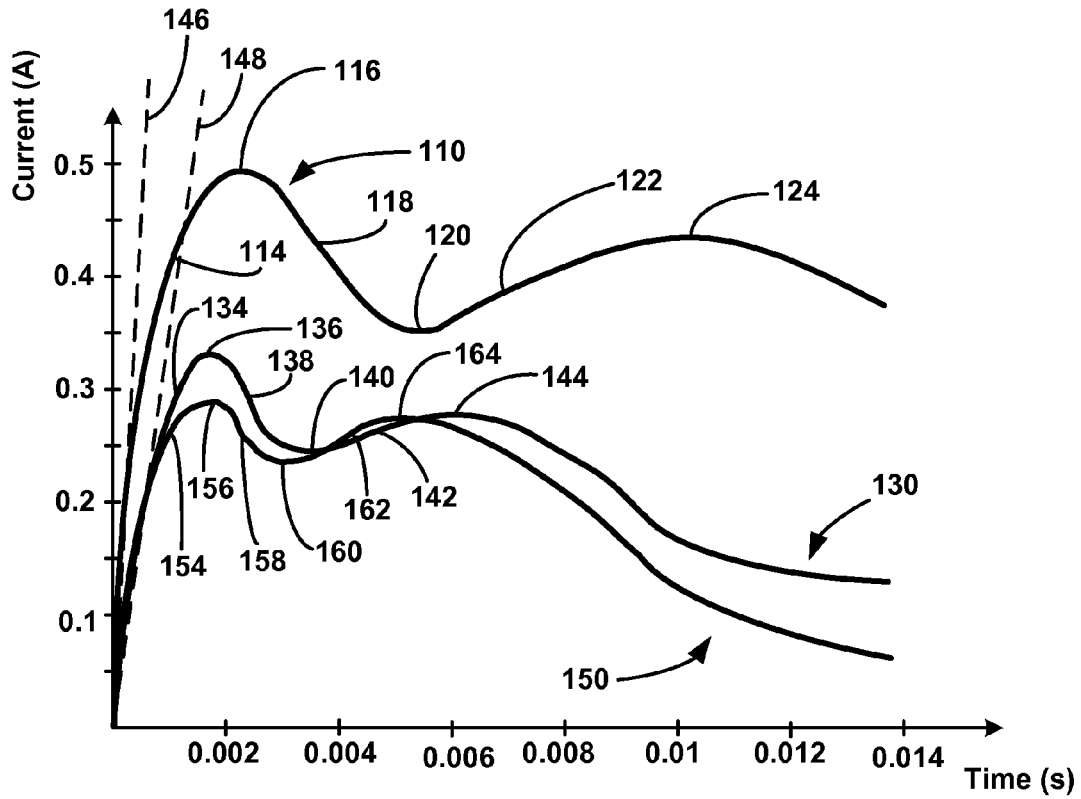
FIG. 6 is a graph showing example current waveforms through a coil of the medical pump for a pump stroke in which no fault condition is present and for pump strokes from a partially-stalled medical pump.

FIGS. 6-11 show examples of current waveforms for other fault conditions that may be experienced by medical pump 40. For example, FIG. 6 shows current waveform 130 (referred to herein as a "first partial stall waveform" 130) for a pump stroke wherein actuator 52 is moved by the current through coil 50, but actuator 52 does not move through a complete pump stroke, referred to herein as a "partial stall" or a "partially-stalled pump." FIG. 6 also includes the example normal current waveform 110 for comparison. As shown in FIG. 6, first partial-stall waveform 130 includes an initial segment 134 where the current increases to an initial peak 136, followed by a segment 138 of decreasing current until a nadir 140 is reached, followed by a rebound segment 142, and a final peak 144. As can be seen in FIG. 6, a partial pump stroke results in an overall reduction in the current at initial peak 136 and at nadir 140 of partial-stroke waveform 130 as compared to initial peak 116 and nadir 120 of normal waveform 110.

A partial pump stroke also results in a reduction in the difference between the current at peak 136 and the current at nadir 140 of partial-stroke waveform 130 as compared to the difference between the current at peak 116 and the current at nadir 120 of normal waveform 110. The initial slope of the current waveforms, also referred to as the current rise rate of change, also decreases for a partial pump stroke, as shown by the comparison between the current rise rate of change for normal waveform 110, represented by line 146, as compared to that of partial-stroke waveform 130, represented by line 146.

FIG. 6 also shows a second waveform 150 (referred to herein as a "second partial-stall waveform" 150) that corresponds to a pump stroke from a partially-stalled pump, wherein the pump stroke that corresponds to second partial-stall waveform 150 occurred at a point in time subsequent to the pump stroke of waveform 130 from the same medical pump 40. Second partial-stall waveform 150 is similar to first partial-stall waveform 130, in that waveform 150 comprises an initial segment 154 where the current increases to an initial peak 156, followed by a segment 158 of decreasing current until a nadir 160 is reached, followed by a rebound segment 162, and a final peak 164. As can be seen in the example of FIG. 6, second partial-stall waveform 150 has a lower initial peak 156 than peak 136 of first partial-stall waveform 130 as well as a smaller difference in current from initial peak 156 to nadir 160, as compared to the difference in current between initial peak 136 and nadir 140 of first partial-stall waveform 130.

In one example, processor 34 may be configured to determine that a partial stall of medical pump 40 has occurred when at least one of, and in some examples combinations of two or more of, the following characteristics of a current waveform exist for a particular pump stroke: a smaller peak current at initial peak 136, 156 compared to an expected peak current for initial peak 116 of a normal waveform 110; a smaller change in current from initial peak 136, 156 to nadir 140, 160 compared to an expected change in current from initial peak 116 to nadir 120 of a normal waveform 110; and an earlier end of stroke time, as indicated by the time of nadir 140, 160 or another inflection point, as compared to an expected end of stroke time indicated by nadir 120 of normal waveform 110.

In one example, processor 34 may be configured to determine the existence of a partial-stall fault condition using only one of the characteristics of a partially-stalled medical pump 40 to determine that a partial-stall fault condition exists, such as only the reduction in initial peak current or only the change in current between the initial peak and the nadir. Processor 34 may also be configured to determine the existence of a partial-stall fault condition using two or more of the characteristics. For example, processor 34 may be configured to determine that a partial stall exists only if a reduction in peak current that indicates a partial stall and a reduction in the change in current between the peak and nadir that indicates a partial both are detected.

Other characteristics may be used in place of or in addition to the current waveform to determine whether a partial stall fault condition exists in medical pump 40. For example, because a partial-stall fault condition results in less energy used for a particular pump stroke, the energy for each pump stroke may be calculated, as described below, such that a decreased energy coupled with a current waveform having a shape similar to waveform 130 or 150 may help processor 34 to confirm that a partial-stall fault condition exists rather than some other type of fault condition. In another example, a partial stall may be detected by determining a retract time of actuator 52 and determining that the retract time corresponds to a partial stall, e.g. because the retract time is smaller than it would be for a full pump stroke. The retract time may be determined by decreasing the time between pump strokes by incremental steps, e.g. by 0.1 milliseconds, 0.5 milliseconds, or 1 millisecond, for each successive stroke. Eventually, if the time between pump strokes is short enough, IMD 12 will instruct pump 40 to begin a new pump stroke before actuator 52 has completed retracting, with will result in a change in the energy calculated for completing the pump stroke, described in more detail below. Other fault conditions may also be detectable by determining a retract time of actuator 52, such as a gas-accumulation fault condition, because retraction of actuator 52 through air will theoretically be faster.

In one example, the current waveforms corresponding to pump strokes for a partially-stalled medical pump 40 go through a progression, such as the example progression shown in FIG. 6 from normal waveform 110, to a first partial-stall waveform 130, to a second partial-stall waveform 150, and possibly to subsequent partial-stall waveforms (not shown). In one example, processor 34 may be configured to recognize the progression from normal waveform 110 to the shape of first partial-stall waveform 130 to the shape of second partial-stall waveform 150, and so on, such as by using any of the techniques described herein, to determine that medical pump 40 is partially stalling. For example, processor 34 may be configured to determine that medical pump 40 is partially stalled, signaling the existence of a fault condition, if a pump stroke having a first partial-stall waveform 130 is detected followed by a pump stroke having a second partial-stall waveform 150 within a predetermined number of pump strokes, such as between about 5 and about 10 pump stokes, immediately following the first detected partial-stall waveform 130.

Figure 7:
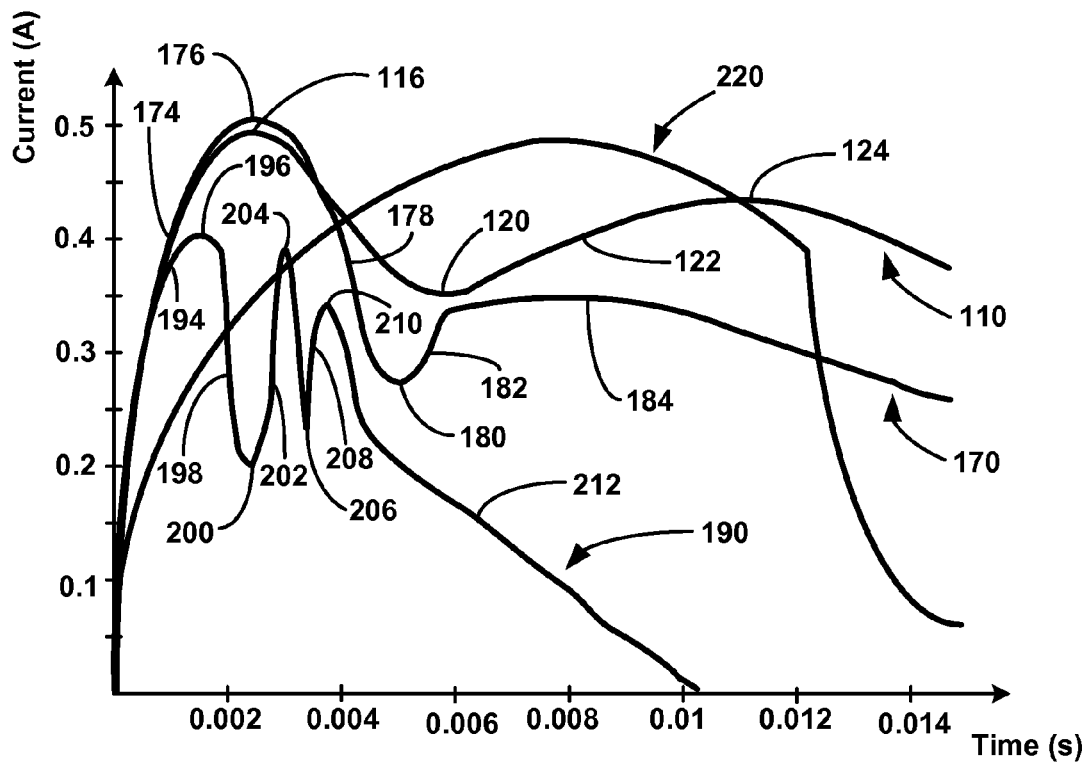
FIG. 7 is a graph showing example current waveforms through a coil of the medical pump for a pump stroke in which no fault condition is present and for pump strokes wherein gas has accumulated within the medical pump.

FIG. 7 shows current waveforms 170, 190, and 220 for a medical pump 40 wherein gas, such as air, has become trapped in the fluid path of medical pump 40, such as by being trapped in chamber 58 or central aperture 62 (FIG. 3), which may eventually lead to the accumulated gas preventing pump from being able to complete a full stroke, referred to herein as an "air-locked pump." FIG. 7 also includes the example normal current waveform 110 for comparison. Current waveform 170 (referred to herein as a "first gas-accumulation waveform 170") corresponds to a pump stroke at a point in time subsequent to the start accumulation of gas within medical pump 40. As shown in FIG. 7, first gas-accumulation waveform 170 includes an initial segment 174 where the current increases to an initial peak 176, followed by a segment 178 of decreasing current until a nadir 180 is reached, followed by a rebound segment 182, and a final peak 184.

As can be seen in the example of FIG. 7, gas accumulation results in nadir 180 of waveform 170, signifying the end of a pump stroke, occurring earlier than nadir 120 of normal waveform 110. The inflection point that occurs at nadir 180 is also sharper compared to the inflection at nadir 120, resulting in a sharper or quicker rebound after the end of the pump stroke. Current waveform 190 (referred to herein as "second gas-accumulation waveform 190") corresponds to a pump stroke at a point in time subsequent to the pump stroke of waveform 170 with the same gas accumulation. Second gas-accumulation waveform 190 includes an initial segment 194 where the current increases to an initial peak 196, followed by a segment 198 of decreasing current until a first nadir 200 is reached, followed by a sharp rebound segment 202, a second peak 204, a sharp current decrease to a second nadir 206, and a second rebound segment 208 to a final peak 210 before settling down for a final declining segment 212.

Additional segments of peaks and nadirs may be possible, depending on the nature of the gas accumulation. The presence of the very sharp inflection of first nadir 200 and the multiple peaks 196, 204, 210 and nadirs 200, 206 before settling into a final declining segment 212, as in waveform 190 of FIG. 7, indicates that the gas accumulation within medical pump 40 is close to leading to an air-locked stall. Current waveform 220 (referred to herein as "air-locked waveform 220") corresponds to a pump stroke at a point in time subsequent to the pump stroke of waveform 190, wherein medical pump 40 has stalled because of the gas accumulation, as referred to as an "air-locked pump." As shown in FIG. 7, air-locked waveform 220 shows no inflection point indicative of the end of a pump stroke, such as a nadir, indicating medical pump 40 has become locked or stalled due to the gas accumulation.

As indicated above, a sharp inflection point at nadir 180, 200 may indicate that there is gas accumulation within medical pump 40. In one example, the width of the trough formed between an initial peak and a second peak, such as initial peak 116 and second peak 124 of normal waveform or initial peak 176, 196 and second peak 184, 204 of gas-accumulation waveforms 170, 190 may be used to determine whether a gas-accumulation fault condition exists. The end points of this trough may be defined by any one of several methods, such as by using the time value at the initial peak as the start point and the second peak as the end point. In another method, the start and end points may be defined by selecting a predetermined current value, such as halfway between the current at the nadir and the current at the second peak. The start point of the trough may be defined as the point when the selected predetermined current is reached along the segment of decreasing current preceding the nadir (e.g., segment 178 of first gas-accumulation waveform 170). The end point of the trough may be defined as the point when the selected predetermined current is reached along the segment of increasing current following the nadir (e.g., segment 182 of first gas-accumulation waveform 170).

Other characteristics may be used in place of or in addition to the current waveform to determine whether a gas-accumulation fault condition exists in medical pump 40. For example, because gas accumulation in medical pump 40 tends to result in less energy required to perform a pump stroke, e.g. because pump 40 is moving a lower volume of the heavier therapeutic agent, the energy for each pump stroke may be calculated, as described below, such that a decreased energy coupled with a current waveform having a shape similar to waveforms 170, 190 or 220 may help processor 34 to confirm that a gas-accumulation fault condition exists rather than some other type of fault condition.

In one example, the current waveforms corresponding to the pump strokes for a medical pump 40 with gas accumulation go through a progression, such as the example progression shown in FIG. 7 from normal waveform 110, to first gas-accumulation waveform 170, to second gas-accumulation waveform 190, and finally to air-locked waveform 220. In one example, processor 34 may be configured to recognize the progression from normal waveform 110 to the shape of first gas-accumulation waveform 170 to the shape of second gas-accumulation waveform 190, and if necessary, to the shape of air-locked waveform 220, such as by using any of the techniques described herein, in order to determine that medical pump 40 has a gas-accumulation fault condition. For example, processor 34 may be configured to determine that medical pump 40 has gas accumulation, signaling the existence of a fault condition, if a pump stroke having a first gas-accumulation waveform 170 indicating gas accumulation is detected followed by a pump stroke having a second gas-accumulation waveform 190 indicating continued gas accumulation within a predetermined number of pump strokes immediately following the first gas-accumulation waveform 170, such as between about 5 and about 10 pump strokes.

Processor 34 may be further configured to determine that a gas-accumulation fault condition exists in medical pump 40 if the second gas-accumulation waveform 190 is followed by a pump stroke having a third gas-accumulation waveform, such as air locked waveform 220, indicating that medical pump 40 continues to have a gas-accumulation fault condition within a predetermined number of pump strokes immediately following the second detected voltage-depleted waveform 190, such as between about 5 and about 10 pump stokes. Processor 34 may use the existence of the progression of waveforms 170, 190, 220 to determine that the fault condition is a gas accumulation fault condition, and not some other fault condition.

Figure 8:
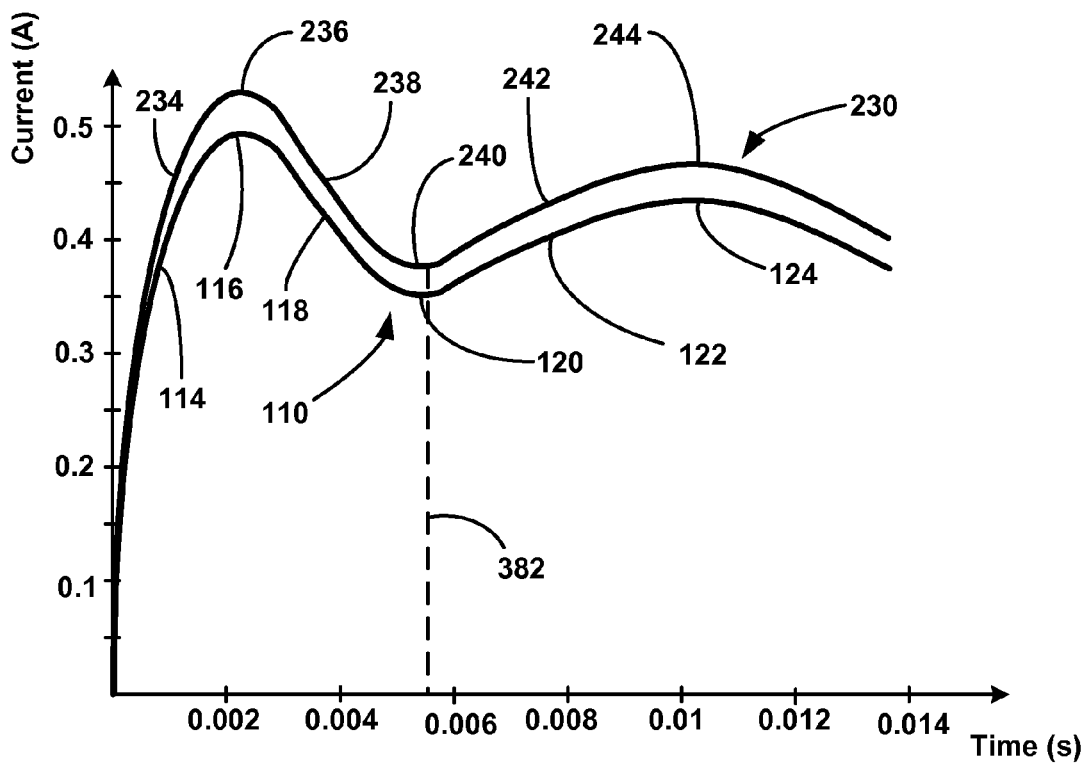
FIG. 8 is a graph showing example current waveforms through a coil of the medical pump for a pump stroke in which no fault condition is present and for a high-energy pump stroke from the medical pump.

FIG. 8 shows a current waveform 230 (referred to herein as "high-energy waveform 230") for a pump stroke from medical pump 40 that required more energy to complete a pump stroke than is considered normal, referred to herein as a "high-energy pump" or a "high-energy pump stroke." A high-energy pump stroke is not, by itself, necessarily the result of a fault condition within medical pump 40. However, in general, a high-energy pump stroke, wherein the energy required for a particular pump stroke or series of pump strokes are above a certain threshold, may be indicative of several fault conditions. A high-energy pump stroke may occur from any condition that resists the motion of actuator 52 so as to result in a higher current draw through coil 50 and a higher energy required to complete the pump stroke. Examples of conditions that may result in a high-energy pump stroke include the presence or accumulation of foreign material between piston 70 and central aperture 62, wear or corrosion within central aperture 62, a portion of return spring 82 being pinched between an actuator surface and a barrier, valve 64 that is stuck closed or partially closed due to accumulation of precipitates or other foreign material, an outlet passage that is occluded, occlusion within catheter 14, such as a kinked or blocked catheter 14, or a blocked inlet filter. FIG. 8 also includes the example normal current waveform 110 for comparison.

As shown in FIG. 8, high-energy waveform 230 includes an initial segment 234 where the current increases to an initial peak 236, followed by a segment 238 of decreasing current until a nadir 240 is reached, followed by a rebound segment 242, and a final peak 244. As with peak 116 and nadir 120 of normal waveform 110, initial peak 236 indicates the point when actuator 52 begins to move and nadir 240 indicates the point when actuator 52 has completed a pump stroke. In the example shown in FIG. 8, the time of initial peak 236 is approximately the same as an expected time of an initial peak 116 of normal waveform 110, the time of nadir 240 is approximately the same as an expected time of nadir 120 of normal waveform 110, and the time of final peak 244 is approximately the same as an expected time of second peak 124 of normal waveform 110. Therefore, in the example of FIG. 8, the primary difference in the shape of high-energy waveform 230 as compared to normal waveform 110 is that each reference point on high-energy waveform 230 is at a higher current then the corresponding point on normal waveform 110, such that there is an offset between the waveforms.

In one example, processor 34 may be configured to determine that a high-energy fault condition exists in medical pump 40 when at least one of the following conditions exists: a higher peak current at initial peak 236 compared to an expected peak current for initial peak 116 of a normal waveform 110; a higher current value at nadir 240 compared to an expected current for nadir 120 of normal waveform 110; and a higher current for second peak 244 compared to an expected current for second peak 124 of normal waveform 110. In one example, processor 34 may be configured to determine the existence of a high-energy fault condition when all three current values, e.g., the current value at initial peak 236, at nadir 240, and at second peak 244, are each higher than the corresponding expected current values for normal waveform 110, e.g., at initial peak 116, at nadir 120, and at second peak 124. In another example, processor 34 may be configured to determine the existence of a high-energy fault condition when all three current values are higher than the corresponding expected current values for normal waveform 110 and when the time at each point, e.g., the time of initial peak 236, the time of nadir 240, and the time of second peak 244, are each approximately the same as the corresponding expected times for normal waveform 110, e.g., the time at initial peak 116, the time at nadir 120, and the time at second peak 124.

Other characteristics may be used in place of or in addition to the current waveform to determine whether a high-energy fault condition exists in medical pump 40. For example, because a high-energy fault condition results in more energy used for a particular pump stroke, the energy for each pump stroke may be calculated, as described below, such that an increased energy coupled with a current waveform having a shape similar to waveform 230 may help processor 34 to confirm that a high-energy fault condition exists rather than some other type of fault condition.

Figure 9:
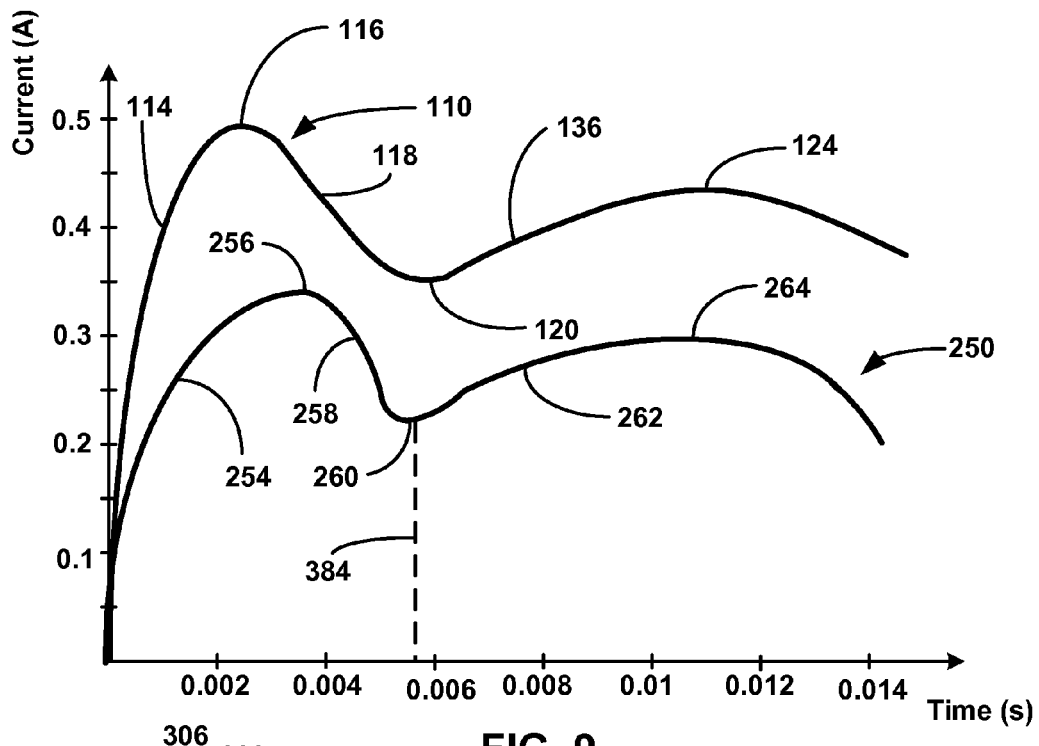
FIG. 9 is a graph showing example current waveforms through a coil of the medical pump for a pump stroke in which no fault condition is present and for a low-energy pump stroke from the medical pump.

FIG. 9 shows a current waveform 250 referred to herein as "low-energy waveform 250") for a pump stroke from medical pump 40 that required less energy to complete a pump stroke than was expected for a normal pump stroke, referred to herein as a "low-energy pump" or a "low-energy pump stroke." A low-energy pump stroke is not, by itself, necessarily the result of a fault condition within medical pump 40. However, in general, a low-energy pump stroke, wherein the energy required for a particular pump stroke or series of pump strokes are below a certain threshold compared to a normal pump stroke, may be indicative of several fault conditions. For example, a low-energy pump stroke may occur when a valve 64 is stuck open, there is air in chamber 58, a defect in return spring 82, such as a fracture, that causes less force to be required to open valve 64, a reduced stroke length of actuator 52, or if actuator 52 is not fully returning and thus only completing a partial stroke. FIG. 9 also includes the example normal current waveform 110 for comparison.

In one example, shown in FIG. 9, low-energy waveform 250 includes an initial segment 254 where the current increases to an initial peak 256, followed by a segment 258 of decreasing current until a nadir 260 is reached, followed by a rebound segment 262, and a final peak 264. As with peak 116 and nadir 120 of normal waveform 110, initial peak 256 indicates the point when actuator 52 begins to move and nadir 260 indicates the point when actuator 52 has completed a pump stroke. Low-energy waveform 250 has a lower current value at initial peak 256 and may be slower in reaching initial peak 256. In one example, a low-energy pump stroke may be shorter than a normal pump stroke, as indicated by the shorter time between peak 256 and nadir 260 of low-energy waveform 250 compared to the time between peak 116 and nadir 120 of normal waveform 110. A low-energy pump stroke may also be indicated by the current value at nadir 260 as compared to the current value at nadir 120 of normal waveform 110.

In one example, processor 34 may be configured to determine that a low-energy fault condition exists in medical pump 40 when at least one of the following conditions exists: a lower peak current at initial peak 256 compared to an expected peak current for initial peak 116 of a normal waveform 110; a lower current value at nadir 260 compared to an expected current for nadir 120 of normal waveform 110; a lower current for final peak 264 compared to an expected current for final peak 124 of normal waveform 110; and a shorter pump stroke indicated by a shorter time between peak 256 and nadir 260 of low-energy waveform 250 compared to an expected time between peak 116 and nadir 120 of normal waveform 110. In one example, processor 34 may be configured to determine the existence of a low-energy fault condition when all three current values, e.g., the current value at initial peak 256, at nadir 260, and at final peak 264, are each lower than the corresponding expected current values for normal waveform 110, e.g., at initial peak 116, at nadir 120, and at second peak 124. In another example, processor 34 may be configured to determine the existence of a low-energy fault condition when all three current values are lower than the corresponding expected current values for normal waveform 110 and when the length of a pump stroke, as indicated by the time between initial peak 256 and nadir 260, is shorter than an expected pump stroke length, as indicated by the expected time between initial peak 116 and nadir 120 of normal waveform 110.

Other characteristics may be used in place of or in addition to the current waveform to determine whether a low-energy fault condition exists in medical pump 40. For example, because a low-energy fault condition results in less energy used for a particular pump stroke, the energy for each pump stroke may be calculated, as described below, such that a decreased energy coupled with a current waveform having a shape similar to waveform 250 may help processor 34 to confirm that a low-energy fault condition exists rather than some other type of fault condition.

Figure 10:
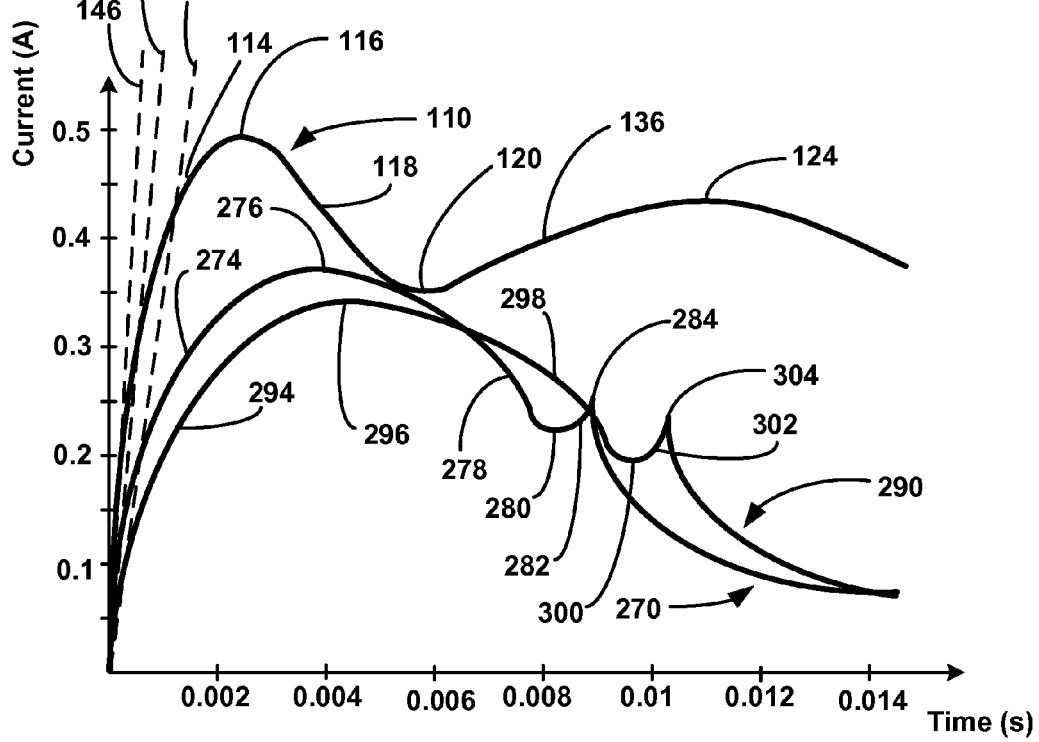
FIG. 10 is a graph showing example current waveforms through a coil of the medical pump for a pump stroke in which no fault condition is present and for pump strokes in which a power source for driving the medical pump has a voltage depletion.

FIG. 10 shows current waveforms 270 and 290 representing a progression of pump strokes due to a depletion of voltage from power source 42, such as from battery 86 (FIG. 4). As described above, waveform 110 corresponds to a normal pump stroke, e.g., wherein the voltage of battery 86 has not been depleted. Current waveform 270 referred to herein as "first voltage-depleted waveform 270") corresponds to a pump stroke at a point in time subsequent to normal waveform 110 where the voltage of battery 86 has been partially depleted. As shown in FIG. 10, first voltage-depleted waveform 270 includes an initial segment 274 where the current increases to an initial peak 276, followed by a segment 278 of decreasing current until a nadir 280 is reached, followed by a rebound segment 282, and a final peak 284. Current waveform 290 referred to herein as "second voltage-depleted waveform 290) corresponds to a pump stroke at a point in time subsequent to waveform 270 where the voltage of battery 86 has been depleted even further. Second voltage-depleted waveform 290 includes an initial segment 294 where the current increases to an initial peak 296, followed by a segment 298 of decreasing current until a nadir 300 is reached, followed by a rebound segment 302, and a final peak 304.

As shown in FIG. 10, as the voltage of power source 42, such as battery 86 or capacitor 88, continues to be depleted the current at the initial peak 276, 296 decreases. The slope of the initial segments, e.g. segments 274, 294, of current waveforms, also referred to as the current rise rate of change, also changes as the voltage of power source 42 is depleted. In the example shown in FIG. 10, the current rise rate of change of normal waveform 110, represented by line 146, has a higher slope than the current rise rate of changes for first depleted-voltage waveform 270, represented by line 306, and for second depleted-voltage waveform 290, represented by line 308. The time until an end of stroke is reached increases as the voltage of power source 42 is depleted, as indicated by nadir 280 of first voltage-depleted waveform 270 occurring later than an expected time of nadir 120 of normal waveform 110, and nadir 300 of second voltage-depleted waveform 290 occurring later than nadir 280 of first voltage-depleted waveform 270.

In one example, processor 34 may be configured to determine that a fault condition corresponding to a voltage-depleted power source 42 exists in medical pump 40 when at least one of the following conditions exists: a lower peak current at initial peak 276, 296 compared to an expected peak current for initial peak 116 of a normal waveform 110; an end-of-stroke time, as indicated by the time at nadir 280, 300, that is later than an expected end-of-stroke time of normal waveform 110, indicated by nadir 120; and a lower current rise rate of change 306, 308 compared to an expected current rise rate of change 146 of a normal waveform 110. In one example, processor 34 may be configured to determine that a fault condition corresponding to a voltage-depleted power source 42 exists in medical pump 40 when all three characteristics indicating a voltage depleted power source 42 exist, e.g., when the current at initial peak 276, 296 is lower than the expected peak current for initial peak 116 of a normal waveform 110, when the end-of-stroke time, as indicated by the time at nadir 280, 300, is later than the expected end-of-stroke time of normal waveform 110, indicated by nadir 120, and when the current rise rate of change 306, 308 is lower than the expected current rise rate of change 146 of a normal waveform 110.

In one example, the current waveforms corresponding to the pump strokes for a medical pump 40 with a voltage-depleted power source 42 go through a progression, such as the example progression shown in FIG. 10 from normal waveform 110, to a first voltage-depleted waveform 270, to a second voltage-depleted waveform 290, and possibly to subsequent voltage depleted waveforms (not shown). In one example, processor 34 may be configured to recognize the progression from normal waveform 110 to the shape of first voltage-depleted waveform 270 to the shape of second voltage-depleted waveform 290, and so on, such as by using any of the techniques described herein, to determine that power source 42 of medical pump 40 has depleted voltage. For example, processor 34 may be configured to determine that power source 42 has a depleted voltage, signaling the existence of a fault condition, if a pump stroke having a first voltage-depleted waveform 270 indicating a depletion of battery voltage is detected followed by a pump stroke having a second voltage-depleted waveform 290 indicating further depletion of the battery voltage within a predetermined number of pump strokes, such as between about 5 and about 10 pump stokes, immediately following the first detected voltage-depleted waveform 270.

Figure 11:
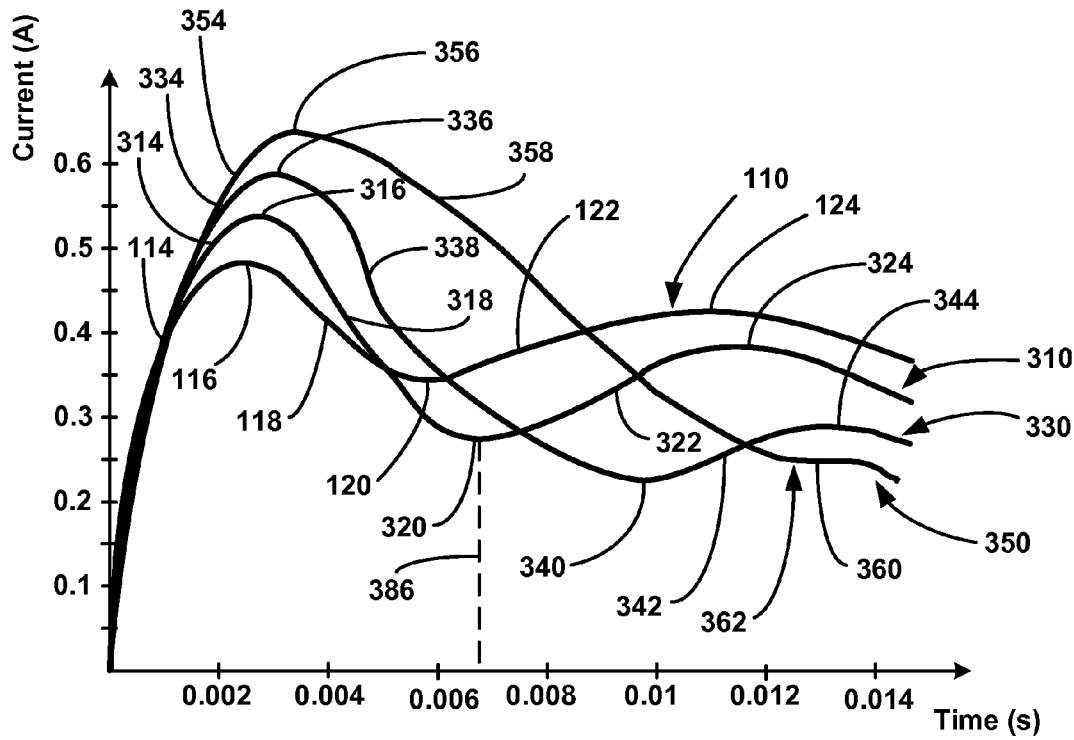
FIG. 11 is a graph showing example current waveforms through a coil of the medical pump for a pump stroke in which no fault condition is present and for pump strokes in which a flow path within the medical pump is blocked.

FIG. 11 shows current waveforms 310, 330 and 350 showing a progression of pump strokes corresponding to blockage within the fluid path after the outlet of medical pump 40, such as a partial or complete blockage at or after one-way valve 64 (described above with respect to FIG. 3). As described above, waveform 110 corresponds to a normal pump stroke, e.g., wherein there is no blockage at the outlet of medical pump 40. Current waveform 310 (referred to herein as "first blocked waveform 310") corresponds to a pump stroke at a point in time subsequent to the formation of a blockage at the outlet of medical pump 40. As shown in FIG. 11, first blocked waveform 310 includes an initial segment 314 where the current increases to an initial peak 316, followed by a segment 318 of decreasing current until a nadir 320 is reached, followed by a rebound segment 322, and a final peak 324. As can be seen in the example of FIG. 11, the blocked pump outlet causes an increase in the current at initial peak 316 compared to the current at initial peak 116 of normal waveform 110, indicating an increase in the energy required to start the pump stroke. Initial peak 316 also occurs at a later time than initial peak 116, indicating that it takes longer to start the pump stroke. As is further shown in FIG. 11, nadir 320 of first blocked waveform 310 occurs at a later point in time and has a slightly lower current value when compared to nadir 120 of normal waveform 110, indicating that it takes longer for medical pump 40 to complete the pump stroke.

Current waveform 330 (referred to herein as "second blocked waveform 330") corresponds to a pump stroke at a point in time subsequent to the pump stroke of waveform 310 with the same blocked outlet. Second blocked waveform 330 includes an initial segment 334 where the current increases to an initial peak 336, followed by a segment 338 of decreasing current until a nadir 340 is reached, followed by a rebound segment 342, and a final peak 344. As can be seen in the example of FIG. 11, the blocked pump outlet causes a further increase in the current at initial peak 336 of second blocked waveform 330 over the already elevated current at initial peak 316 of first blocked waveform 310, and initial peak 336 of second blocked waveform 330 occurs at a later time than initial peak 316 of first blocked waveform 310. This indicates that medical pump 40 requires more and more energy to start successive pump strokes when the pump outlet is blocked. As is further shown in FIG. 11, nadir 340 of second blocked waveform 330 occurs at a later point in time and has a lower current value than nadir 320 of first blocked waveform 310. This indicates that it takes longer and longer for medical pump 40 to complete successive pump strokes when pump outlet is blocked.

Current waveform 350 (referred to herein as "third blocked waveform 350") corresponds to a pump stroke at a point in time subsequent to the pump stroke of second blocked waveform 330 with the same blocked outlet. Third blocked waveform 350 includes an initial segment 354 where the current increases to an initial peak 356, followed by a segment 358 of decreasing current. Third blocked waveform 350 does include an inflection point 360 within a segment 362 where the current flattens out slightly, but it is difficult to detect compared to nadirs 320, 340. Third blocked waveform 350 does not include a rebound segment or a final peak.

As can be seen in the example of FIG. 11, the blocked pump outlet continues to cause an increase in the current at initial peak 356 of third blocked waveform 350 compared to initial peak 336 of second blocked waveform 330, and initial peak 356 of third blocked waveform 350 occurs at a later time than initial peak 336 of second blocked waveform 330. This further indicates that medical pump 40 continues to require more and more energy to start successive pump strokes when the pump outlet is blocked. The inflection point 360 in segment 362, indicating an end of the pump stroke, occurs at a later point in time and has a lower current value than nadir 340 that indicates the end of the pump stroke of second blocked waveform 330, further indicating that it takes longer and longer for medical pump 40 to complete successive pump strokes when pump outlet is blocked.

Although not shown in FIG. 11, at a time after third blocked waveform 350, medical pump 40 may become fully blocked such that it ceases to create a pump stroke. In such a case, the current waveform that corresponds to an attempted pump stroke may resemble waveform 126 (FIG. 5) corresponding to a fully stalled pump.

In one example, processor 34 may be configured to determine that a fault condition corresponding to a blocked outlet of medical pump 40 exists when at least one of the following conditions exists: a higher peak current at initial peak 316, 336, 356 compared to an expected peak current for initial peak 116 of a normal waveform 110; a start-of-stroke time, as indicated by the time at initial peak 316, 336, 356, that is later than an expected start-of-stroke time of normal waveform 110, indicated by initial peak 116; an end-of-stroke time, as indicated by the time at nadir 320, 340 or inflection point 360, that is later than an expected end-of-stroke time of normal waveform 110, indicated by nadir 120; and a lower current value at nadir 320, 340 or inflection point 360 compared to an expected current for nadir 120 of normal waveform 110.

In one example, processor 34 may be configured to determine that a fault condition corresponding to a blocked outlet exists when all four characteristics indicating a blocked outlet are detected, e.g., when the current at initial peak 316, 336, 356 is higher than the expected peak current for initial peak 116 of a normal waveform 110, when the start-of-stroke time, as indicated by the time at initial peak 316, 336, 356, is later than the expected start-of-stroke time of normal waveform 110, indicated by initial peak 116, when the end-of-stroke time, as indicated by the time at nadir 320, 340 or inflection point 360, is later than the expected end-of-stroke time of normal waveform 110, indicated by nadir 120, and when the current value at nadir 320, 340 or inflection point 360 is lower than the expected current value at nadir 120 of normal waveform 110.

Other characteristics may be used in place of or in addition to the current waveform to determine whether medical pump 40 has a blocked outlet. For example, because a blocked outlet tends to cause the energy required to complete a pump stroke to increase, the energy for each pump stroke may be calculated, as described below, such that detection of an increased energy coupled with a current waveform having a shape similar to waveforms 310, 330, or 350 may help processor 34 to confirm that a blocked-outlet fault condition exists rather than some other type of fault condition. In one example, IMD 12 may also include a pressure sensor 364 at the outlet of medical pump 40 (shown schematically in FIG. 2), in order to detect the outlet pressure of medical pump 40. When medical pump 40 has a blocked outlet, the outlet pressure measured by pressure sensor 364 is increased compared to the outlet pressure for an unblocked medical pump. In one example, processor 34 may be configured to analyze the outlet pressure recorded by pressure sensor 364 in place of or in conjunction with the current through coil 50 in order to determine that medical pump 40 is blocked. In one example, processor 34 uses a drop in outlet pressure, as recorded by pressure sensor 364, coupled with a current waveform having a shape similar to waveforms 310, 330, 350, to confirm that a blocked-outlet fault condition exists rather than some other type of fault condition.

In one example, the current waveforms corresponding to pump strokes for a medical pump 40 having a blocked outlet go through a progression, such as the example progression shown in FIG. 11 from normal waveform 110, to a first blocked waveform 310, to a second blocked waveform 330, to third blocked waveform 350, and possibly to subsequent blocked outlet waveforms (not shown). In one example, processor 34 may be configured to recognize the progression from normal waveform 110 to the shape of first blocked waveform 310 to the shape of second blocked waveform 330 to the shape of third blocked waveform 350, and so on, such as by using any of the techniques described herein, to determine that medical pump 40 has a blocked outlet. For example, processor 34 may be configured to determine that pump 40 has a blocked outlet, signaling the existence of a fault condition, if a pump stroke having a first blocked waveform 310 is detected followed by a pump stroke having a second blocked waveform 330 within a predetermined number of pump strokes, such as between about 5 and about 10 pump stokes, immediately following the first blocked waveform 310.

In another example, processor 34 may be configured to determine that pump 40 has a blocked outlet if a pump stroke having a first blocked waveform 310 is detected followed by a pump stroke having a second blocked waveform 330 within a predetermined number of pump strokes, such as between about 5 and about 10 pump stokes, immediately following the first blocked waveform 310, followed by a pump stroke having a third blocked waveform 350 within a predetermined number of pump strokes, such as between about 5 and about 10 pump strokes, immediately following the second blocked waveform 330.

In one example, IMD 12 is configured to monitor each pump stroke and determine if a particular pump stroke or series of pump strokes corresponds to a fault condition within medical pump 40. IMD 12 may be configured to detect a property associated with the energy required to energize coil 50 to drive actuator 52 through a pump stroke and to determine if the property associated with the energy required to energize coil 50 indicates that a fault condition exists with the medical pump 40. In one example, a sensor is provided within IMD to detect or measure the property associated with the energy required to energize coil 50, and processor 34 is configured to determine if the property associated with the energy required to energize coil 50 indicates the existence of a fault condition.

Examples of properties that are associated with the energy required to move actuator 52 through a pump stroke that may be used to determine if a fault condition exists include a shape of a current waveform through the actuation mechanism when the actuation mechanism is energized to provide a pump stroke, a total energy supplied to the actuation mechanism in order to produce a pump stroke, a voltage change across the actuation mechanism during a pump stroke, an outlet fluid pressure of the medical pump, a current value at an initial peak of a current waveform, a current value at a nadir of a current waveform, a difference in current between an initial peak and a nadir of a current waveform, an initial current rise rate of change of a current waveform, the time at which an initial peak of a current waveform occurs (e.g., the time at which actuator 52 begins to move), the time at which a nadir of a current waveform occurs (e.g., the time at which actuator 52 completes a pump stroke), the difference in time between an initial peak and a nadir of a current waveform (e.g., the time from the start to the finish of a pump stroke), and the shape of an inflection point, such as a nadir, of a current waveform.

In one example, IMD 12 is configured to analyze the waveforms of each pump stroke and to determine if the waveform is associated with a normal pump stroke, e.g., a pump stroke wherein no fault condition exists, or a waveform that indicates that a fault condition exists within medical pump 40. In one example, IMD 12 may also be configured to determine what type of fault condition exists in order to initiate a recovery to remedy the fault condition or to inform a user, such as the patient or a physician, of the existence of the fault condition, or both. IMD 12 may be configured to analyze the features of the waveforms described above, such as: the time of the initial peak 116, 136, 156, 176, 196, 236, 256, 276, 296, 316, 336, 356; the current at initial peak 116, 136, 156, 176, 196, 236, 256, 276, 296, 316, 336, 356; the length and slope of initial segment 114, 134, 154, 174, 194, 234, 254, 274, 294, 314, 334, 354; the length and slope of the decreasing-current segment 118, 138, 158, 178, 198, 238, 258, 278, 298, 318, 338. 358 (e.g., the difference in time between initial peak 116, 136, 156, 176, 196, 236, 256, 276, 296, 316, 336, 356 and nadir 120, 140, 160, 180, 200, 240, 260, 280, 320, 340 or inflection point 360); the time of nadir 120, 140, 160, 180, 200, 240, 260, 280, 320, 340 or inflection point 360; the current value at nadir 120, 140, 160, 180, 200, 240, 260, 280, 320, 340 or inflection point 360; the shape of nadir 120, 140, 160, 180, 200, 240, 260, 280, 320, 340 or inflection point 360; whether an inflection point such as nadir 120, 140, 160, 180, 200, 240, 260, 280, 320, 340 or inflection point 360 is present; the existence of multiple peaks and nadirs, such as peaks 196, 204, and 210 and nadirs 200 and 206 of current waveform 190 (FIG. 7); the initial current rise rate of change 146, 148, 306, 308, or any other characteristic that may be used to determine if a fault condition exists within medical pump 40.

Figure 12:
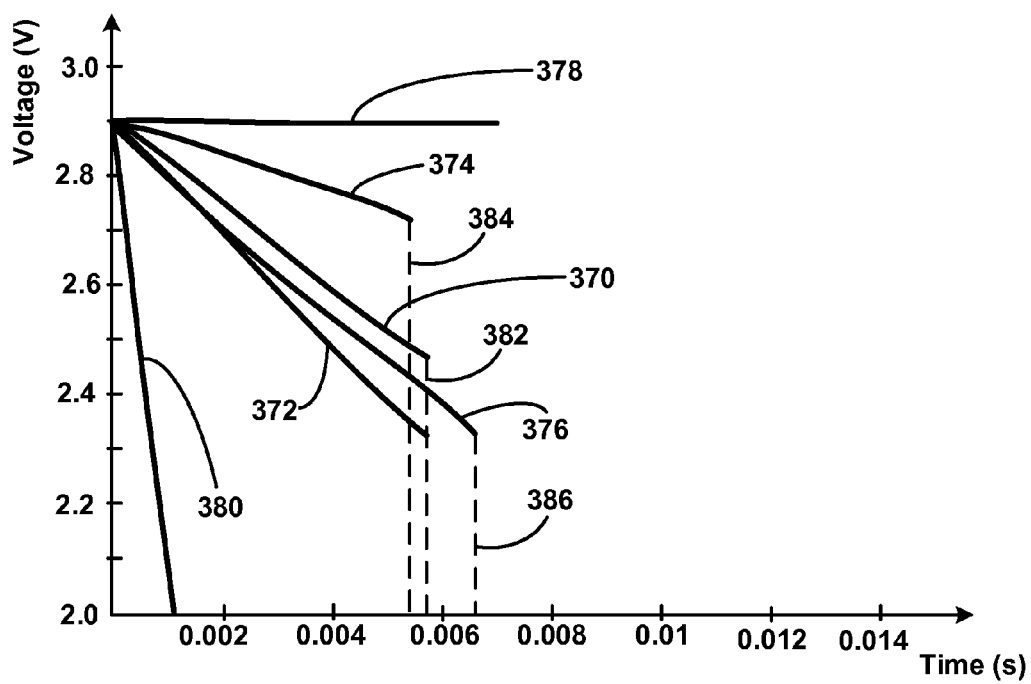
FIG. 12 is a graph showing example voltage waveforms across a coil of the medical pump for a pump stroke when no fault condition exists and for pump strokes in which various fault conditions exist within the medical pump.

As described above with respect to FIGS. 5-11, the current waveform of pump strokes may be used to determine whether a fault condition exists. However, other properties may be used in place of or in addition to the current waveform in order to determine that a particular pump stroke indicates a fault condition within medical pump 40. For example, the shape of a voltage waveform may be used to determine whether certain fault conditions exists. FIG. 12 shows examples of waveforms for the voltage across coil 50 that corresponds to the several examples of pump strokes or attempted pump strokes. A voltage waveform also may be used alone or in conjunction with the current waveform to determine the amount of energy provided to coil 50 during the pump stroke. The measured voltage across coil 50, referred to herein as $V_{Coil}$, can be used to calculate the total energy that passes through coil 50 during a specific time. When energy is being provided by a capacitor, such as capacitor 88, and it can be assumed that the capacitance of the capacitor is constant, the energy provided to coil 50 from capacitor 88, $W_{Coil}$, can be calculated according to Equation 1:

$$W_{Coil} = \frac{1}{2} C(V_{Coil,Start}^2 - V_{Coil,End}^2) \quad [1]$$

Where C is the capacitance of capacitor 88, $V_{Coil,Start}$ is the voltage across coil 50 at the start of the pump stroke and $V_{Coil,End}$ is the voltage across coil 50 at the end of the pump stroke. IMD 12 may be configured so that the energy provided to coil, $W_{Coil}$, is calculated for each pump stroke so that it can be determined whether the energy provided to coil 50 corresponds to a high-energy normal pump stroke, or a low-energy pump stroke. In one example, the capacitance of capacitor 88 is measured and stored in memory 36 so that an accurate energy calculation using Equation 1 can be made.

FIG. 12 includes example voltage waveforms 370, 372, 374, 376, 378, and 380, each corresponding to several examples of pump strokes or attempted pump strokes. Example voltage waveforms 370, 372, 374, and 376 are examples of the voltage across coil 50 for several completed pump strokes, including a normal pump stroke and several pump strokes from a pump 40 where a fault condition exists. Example voltage waveforms 378 and 380 are examples of the voltage across coil 50 when a pump stroke was instructed, e.g. attempted by processor 34, but where no pump stroke occurred.

Voltage waveform 378, for example, represents the voltage across coil when capacitor 88 is not connected to coil 50 for some reason, such as because of a broken connection in the coil wire, coil connector, or a circuit board between capacitor 88 and coil 50, sometimes referred to as an "open coil." Voltage waveform 380 represents the case where a short circuit has developed in coil 50, such as through undesired contact between adjacent windings within coil 50. As can be seen in FIG. 12, a shorted coil 50 causes a sharp decline in voltage at a much faster rate than a normal pump stroke or even in a high-energy pump stroke.

Waveform 370 is an example of the voltage across coil 50 during a normal pump stroke, waveform 372 is an example of the voltage across coil 50 during a high-energy pump stroke, waveform 374 is an example of the voltage across coil 50 during a low-energy pump stroke, and waveform 376 is an example of the voltage across coil 50 during a pump stroke where the outlet of medical pump 40 is partially blocked. For ease of discussion, voltage waveform 370 results from the same normal pump stroke that produced current waveform 110 in FIGS. 5-11, voltage waveform 372 results from the same high-energy pump stroke that produced current waveform 230 in FIG. 8, voltage waveform 374 results from the same low-energy pump stroke that produced current waveform 250 in FIG. 9, and voltage waveform 376 results from the same blocked-outlet pump stroke that produced current waveform 310 in FIG. 11.

IMD 12 may also include means for determining when actuator 52 has reached the end of a pump stroke, such that switching device 92 may be opened as soon as the end of stroke is detected in order to conserve energy. As shown in the examples of FIG. 12, IMD 12 has determined that the normal pump stroke of voltage waveform 370 and current waveform 110 (FIG. 5) occurred at the time represented by line 382, that the end of the high-energy pump stroke of voltage waveform 372 and current waveform 230 (FIG. 8) also occurred at the time represented by line 382, that the low-energy pump stroke of voltage waveform 374 and current waveform 250 (FIG. 9) occurred at the time represented by line 384, and that the blocked-outlet pump stroke of voltage waveform 376 and current waveform 310 (FIG. 11) occurred at the time represented by line 386.

In the examples of FIG. 12, coil voltage sensor 102 (FIG. 4) can be used to determine the values that will be used in Equation 1. As shown in the examples of FIG. 12, the starting voltage, $V_{Coil,Start}$, for each voltage waveform is approximately the same, but the ending voltages are different. As is apparent from Equation 1, a higher ending voltage results in a lower amount of energy dissipated through coil, while a lower ending voltage results in a higher amount of energy dissipated through coil. It can be seen from the examples of FIG. 12, that a normal pump stroke, with a corresponding normal voltage waveform 370, results in a higher amount of energy required than a low-energy pump stroke with a corresponding voltage waveform 376, but the normal pump stroke results in a lower energy requirement than a high-energy pump stroke or a blocked-outlet pump stroke.

In another example, not shown, processor 34 may determine that the starting voltage for a waveform corresponding to a first pump stroke is different, within an acceptable tolerance, than the starting voltage for a waveform corresponding to a second pump stroke. The difference in starting voltages correspond to a fault condition within the charging circuit for charging capacitor 88, such as the example charging circuit shown in FIG. 4.

In another example, the energy supplied to coil 50 can be calculated by using coil current sensor 100 in conjunction with coil voltage sensor 102 to determine the total energy required for each pump stroke. In such examples, instead of employing Equation 1, the energy across coil 50, $W_{Coil}$, may be calculated according to Equation 2.

$$W_{Coil} = \int_{t1}^{t2} V_{Coil}(t) \cdot I_{Coil}(t) dt \qquad [2]$$

As can be seen, Equation 2 requires integration of the product of two time-varying functions, $V_{Coil}(t)$ and $I_{Coil}(t)$. As described above, IMD 12 may include an analog-to-digital converter (ADC) 138 that can convert the analog output from coil current sensor 100 to a digital output that can be analyzed by a processor, such as processor 34 of IMD 12 or a processor of external programmer 20, to determine if a fault condition exists. ADC 138 may also be used to convert an analog output from coil voltage sensor 102 to a digital output. The digital outputs of the current values from coil current sensor 100 and coil voltage sensor 102 can be used by processor 34 to perform the integration of Equation 2 in order to calculate the energy that is provided to coil 50. An analog integration may also be performed.

In one example, the energy across coil 50, $W_{Coil}$, may be calculated for each pump stroke and stored in memory 36 to form an energy history of pump 40. $W_{Coil}$ for the history may be calculated using either Equation 1 or Equation 2 described above. The energy history of pump 40 can be used by processor 34, or another processor on another computing device such as programmer 20, to analyze the pump strokes performed by pump 40 over time, which may allow the processor to determine if a fault condition has occurred or is likely to occur in the near future.

In one example, IMD 12 is configured to store the actual shape of the current waveform and/or voltage waveform of a pump stroke in memory 36 such that processor 34 can analyze the waveform shape for each pump stroke. In one example, an analog-to-digital converter (ADC) 138 (FIG. 4) converts the output signal from coil current sensor 100 into a digital output that can be stored in memory 36 and analyzed by a processor, such as processor 34 (as shown in FIG. 4) or a processor of an external device, such as the processor of external programmer 20. Once the waveforms of each pump stroke have been converted by ADC 138, the digital values representative of the waveforms may be analyzed by the processor, such as by comparing the shape of the waveform of each pump stroke to expected, baseline waveform shapes, or by analyzing landmarks of each pump stroke waveform to determine if the waveform has a shape or other characteristics that corresponds to a normal waveform, such as normal waveform 110 shown in FIGS. 5-11, or a shape or other characteristics that correspond to a fault condition, such as full stall waveform 126 of FIG. 5, partial stall waveforms 130, 150 of FIG. 6, gas-accumulation waveforms 170, 190 or air-locked waveform 220 of FIG. 7, high-energy waveform 230 of FIG. 8, low-energy waveform 250 of FIG. 9, waveforms 270 and 290 that indicate depletion of the voltage of battery 86, as in FIG. 10, and waveforms 310, 330, 350 that indicate a blocked outlet of medical pump 40, as in FIG. 11.

Figure 13:
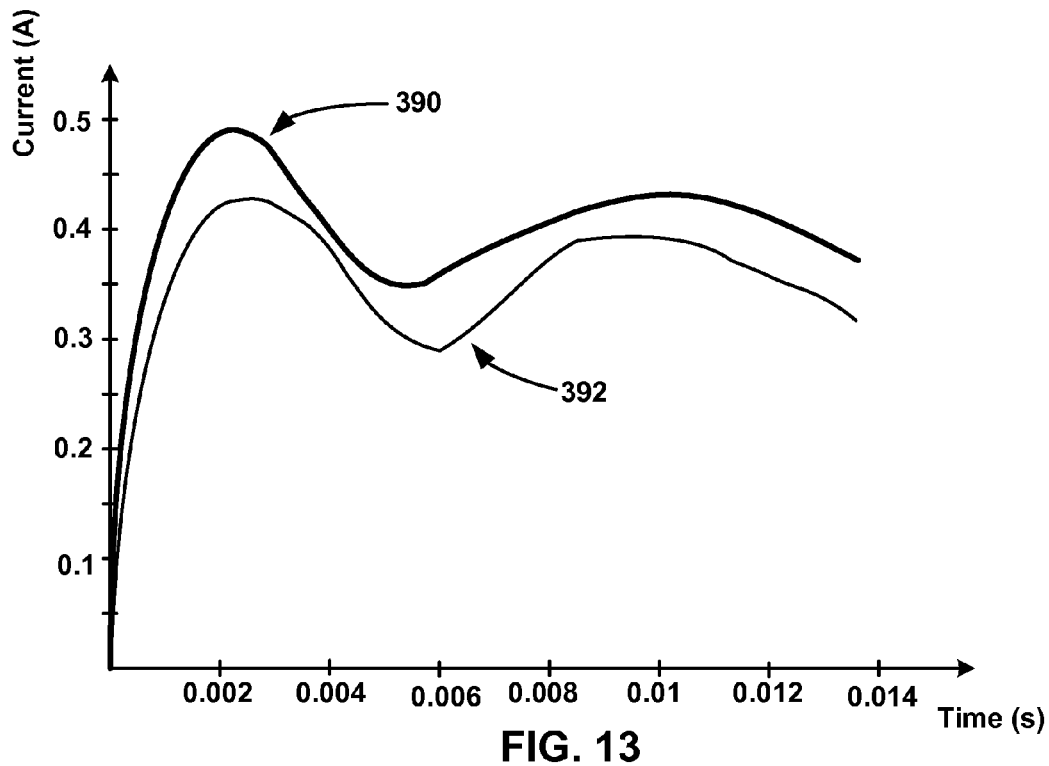
FIG. 13 is a graph showing an example current baseline waveform and an example actual current waveform through a coil corresponding to a pump stroke in which no fault condition exists.

In one example, processor 34 may analyze the waveform of a particular pump stroke by comparing digital values representative of the waveform to stored digital values representative of a baseline waveform. For example, a normal pump stroke baseline waveform and one or more baseline waveforms for each fault condition may be created prior to the implantation or initial programming of IMD 12 and stored on memory 36. Processor 34 may be configured to analyze and compare the waveform shape of each pump stroke to the baseline waveforms to determine if the particular waveform corresponds to normal stroke baseline waveform, and hence a normal pump stroke, or to a baseline waveform corresponding to a fault condition. In one example, shown in FIG. 13, a normal pump stroke baseline waveform 390 is stored in memory 36. FIG. 13 also shows a waveform 392 that results from an actual normal pump stroke. Processor 34 may compare actual waveform 392 to baseline waveform 390 and determine that actual waveform 392 is similar to baseline waveform 390, within an acceptable tolerance, as described in more detail below, such that processor 34 determines that actual waveform 392 corresponds to a normal pump stroke.

Figure 14:
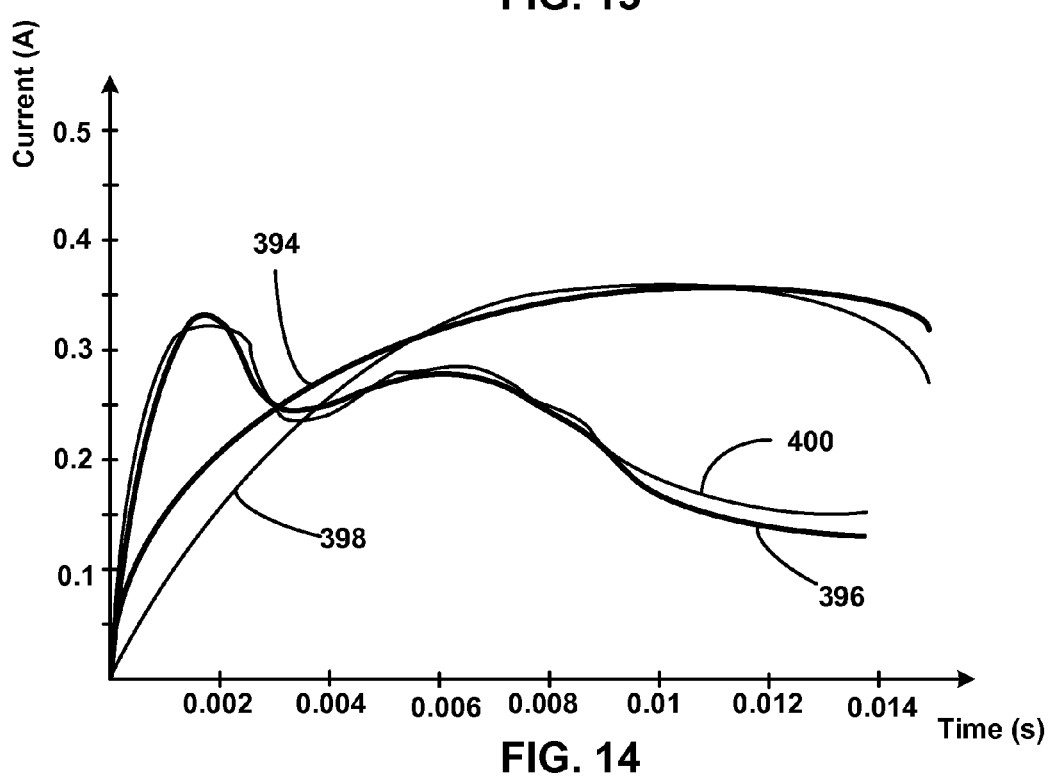
FIG. 14 is a graph showing example current baseline waveforms and example actual current waveforms through a coil corresponding to a fully-stalled medical pump and a partially-stalled medical pump.

Baseline waveforms corresponding to each type of fault condition may also be created and stored on IMD 12. For example, FIG. 14 shows a baseline waveform 394 that corresponds to a stalled pump along with a baseline waveform 396 that corresponds to a partially-stalled pump. FIG. 14 also shows an actual waveform 398 that resulted from an attempted pump stroke from a stalled pump and an actual waveform 400 that resulted from a partially-stalled pump.

Figure 15:
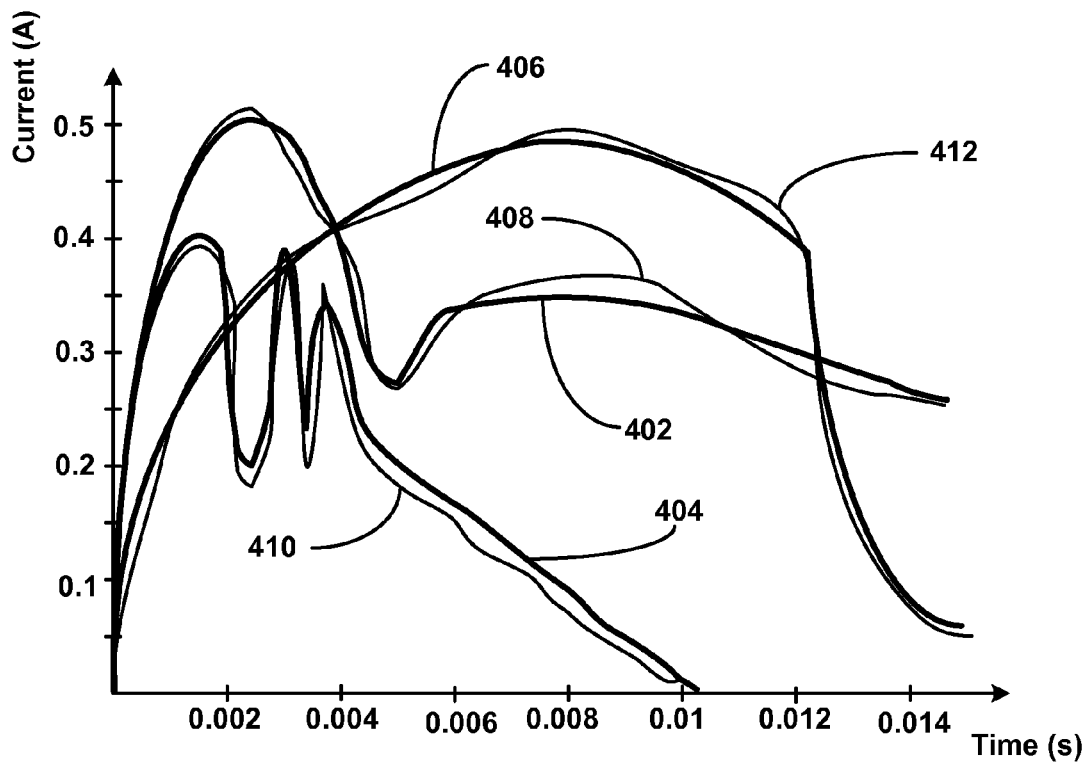
FIG. 15 is a graph showing example current baseline waveforms and example actual current waveforms through a coil corresponding to gas accumulation within the medical pump.

FIG. 15 shows a first baseline waveform 402 that corresponds to an initial pump stroke that corresponds to gas accumulation in medical pump 40. FIG. 15 also includes a second baseline waveform 404 that corresponds to a subsequent pump stroke from the same gas accumulation within the same medical pump 40 near, but prior to, the time when the gas accumulation causes medical pump 40 to become air locked. FIG. 15 further includes a baseline waveform 406 that corresponds to the expected waveform for medical pump 40 when it has become air locked due to gas accumulation. FIG. 15 also shows an actual waveform 408 that resulted from a first pump stroke with gas accumulation in medical pump 40, an actual waveform 410 that resulted from a second pump stroke subsequent to the first pump stroke with the same gas accumulation in medical pump 40, and an actual waveform 412 that resulted from an attempted pump stroke from an air-locked medical pump 40 subsequent to the second pump stroke.

Figure 16:
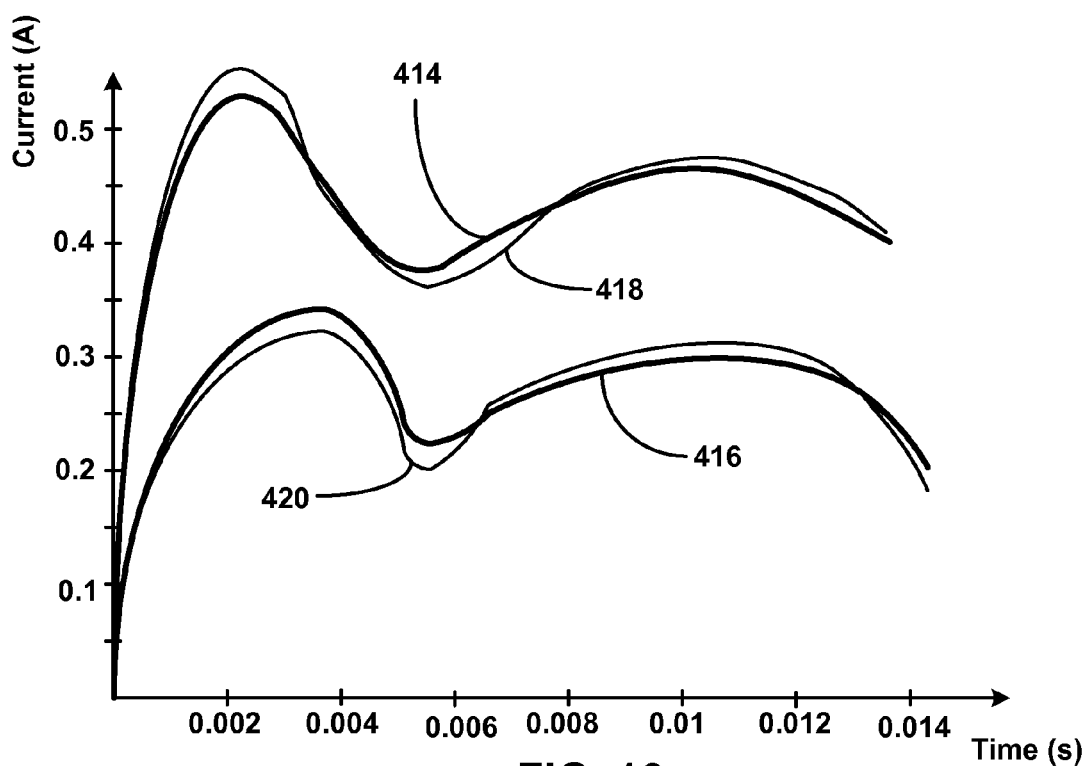
FIG. 16 is a graph showing example current baseline waveforms and example actual current waveforms through a coil corresponding to a high-energy pump stroke and a low-energy pump stroke from the medical pump.

FIG. 16 shows a baseline waveform 414 that corresponds to a high-energy pump stroke of medical pump 40 and a baseline waveform 416 that corresponds to a low-energy pump stroke of medical pump 40. FIG. 16 also includes an actual waveform 418 that resulted from a high-energy pump stroke, such as from a a kink in catheter 14, a valve that is sticking closed, or foreign matter accumulation within central aperture 62, and an actual waveform 420 that resulted from a low-energy pump stroke, such as from a valve is stuck open or from air in chamber 58 or a partial pump stroke.

Figure 17:
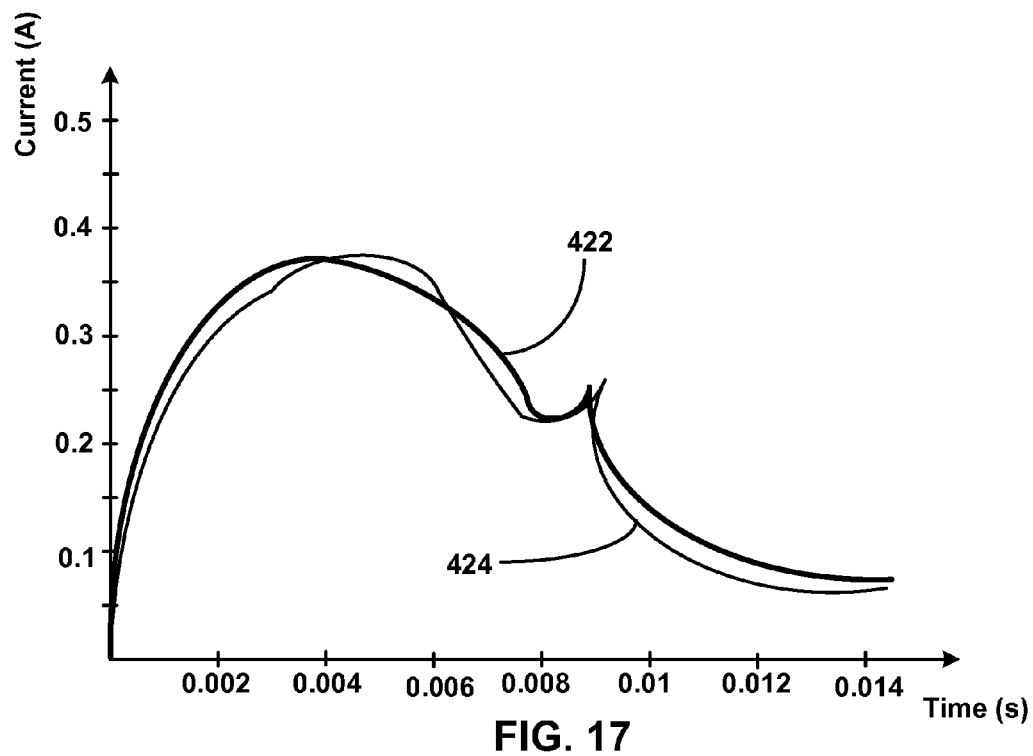
FIG. 17 is a graph showing an example current baseline waveform and an example actual current waveform through a coil corresponding to a pump stroke from a medical pump having a voltage-depleted power source.

FIG. 17 shows a baseline waveform 422 that corresponds to a pump stroke from medical pump 40 having a voltage-depleted battery 86. FIG. 17 also includes an actual waveform 424 that resulted from a pump stroke from voltage-depleted medical pump 40.

Figure 18:
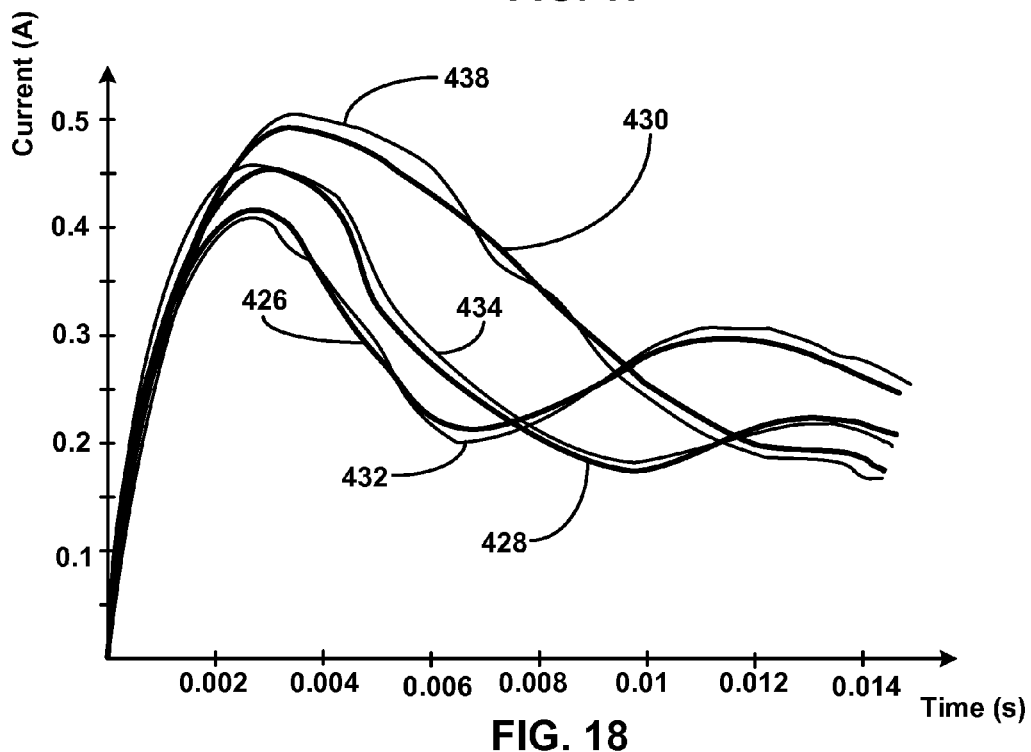
FIG. 18 is a graph showing example current baseline waveforms and example actual current waveforms through a coil corresponding to a blockage within a flow path of the medical pump.

FIG. 18 shows a first baseline waveform 426 that corresponds to a first pump stroke from a medical pump 40 having a blocked outlet. FIG. 18 also includes a second baseline waveform 428 that corresponds to a second pump stroke subsequent to the first pump stroke and a third baseline waveform 430 that corresponds to a third pump stroke subsequent to the second pump stroke from the same blocked medical pump 40. FIG. 18 also shows an actual waveform 432 that resulted from a first pump stroke with a medical pump 40 having a blocked outlet, an actual waveform 434 that resulted from a second pump stroke subsequent to the first pump stroke with the same blocked medical pump 40, and an actual waveform 436 for a third pump stroke subsequent to the second pump stroke that resulted from the same blocked medical pump 40.

Processor 34 may compare the resulting actual waveform from each pump stroke to the baseline waveforms stored in memory 36, such as baseline waveforms 390, 394, 396, 402, 404, 406, 414, 416, 422, 426, 428, and 430 and determine whether a particular actual waveform corresponds to one of the stored baseline waveforms. For example, if a pump stroke results in an actual waveform 392 (FIG. 13), processor 34 may determine that actual waveform 392 is similar to baseline waveform 394, within an acceptable tolerance, as described in more detail below, such that processor 34 determines that actual waveform 392 corresponds to a normal pump stroke. Similarly, if a pump stroke results in an actual waveform 422 (FIG. 17), then processor 34 may determine that actual waveform 422 corresponds to baseline waveform 424, and thus may determine that the pump stroke of actual waveform 422 corresponds to a voltage-depleted battery 86 in medical pump 40.

Baseline waveforms, such as the example baseline waveforms 390, 394, 396, 402, 404, 406, 414, 416, 422, 426, 428, and 430 shown in FIGS. 13-18, may be created at a time prior to the operation of IMD 12 within patient 1. For example, normal pump stroke baseline waveform 390 may be created at the time of manufacture of IMD 12 or at a time before IMD 12 is implanted in patient 1, such as by filling reservoir 30 with a fluid and performing a pump stroke under controlled conditions in order to create a current waveform that will be used as baseline waveform 390 for a normal pump stroke. The resulting baseline waveform 390 may then be stored in memory 36 for use during operation of pump 40. Similarly, stall baseline waveform 394 (FIG. 14), partial stall baseline waveform 396 (FIG. 14), gas-accumulation baseline waveforms 402 and 404 (FIG. 15), air-locked baseline waveform 406 (FIG. 15), high-energy baseline waveform 414 (FIG. 16), low-energy baseline waveform 416 (FIG. 16), voltage-depleted baseline waveform 422 (FIG. 17), and blocked-outlet baseline waveforms 426, 428, 430 (FIG. 18) also may be created at the time of manufacture of IMD 12 or at another time before IMD 12 is implanted by performing a pump stroke under controlled conditions for each pump stroke type, e.g., by creating each fault condition within the particular IMD 12 being programmed, and storing the resulting waveforms as baseline waveforms 390, 394, 396, 402, 404, 406, 414, 416, 422, 426, 428, and 430 in memory 36. Baseline waveforms 390, 394, 396, 402, 404, 406, 414, 416, 422, 426, 428, and 430 may also be determined based on the design of IMD 12 and then saved in memory 36. Baseline waveforms 390, 394, 396, 402, 404, 406, 414, 416, 422, 426, 428, and 430 could also be created by a clinician performing programming of IMD 12, such as via external programmer 20, using similar methods.

Although each baseline waveform 390, 394, 396, 402, 404, 406, 414, 416, 422, 426, 428, and 430 shown in FIGS. 13-18 are shown as a single waveform line, the term "baseline waveform," as it is used herein, may include a set of waveform shapes or a range of baseline waveform shapes for each fault condition that are analyzed and compared to the waveform shape of each pump stroke. For example, partial-stall baseline waveform 396 (FIG. 14) may comprise a plurality of waveform shapes that together form a range of waveform shapes that correspond to partial stalls within medical pump 40. The waveform shape of each pump stroke may be analyzed such that if the actual pump stroke waveform shape falls within the range of partial-stall baseline waveform 396, the pump stroke will be determined to correspond to a partially-stalled pump 40. Similar ranges of baseline waveform shapes may be created and stored for each type of fault condition, including, for example, a fully-stalled fault condition, a gas accumulation fault condition, an air-locked fault condition, a high-energy fault condition, a low-energy fault condition, a voltage-depleted battery fault condition, and a blocked outlet fault condition.

IMD 12 may be configured to store the waveform of each pump stroke in order to compare to the baseline waveforms 390, 394, 396, 402, 404, 406, 414, 416, 422, 426, 428, and 430. In one example, IMD 12 stores the waveform of each pump stroke by storing the digital values of the current through coil 50 as a function of time, as measured by coil current sensor 100 and converted by ADC 138, in memory 36. IMD 12 may also store the baseline waveforms as a series of current values as a function of time. For example, FIG. 13 shows a visual representation of an actual waveform 392 of a recent pump stroke that is stored on memory 36. Even though baseline waveform 390 and actual waveform 392 are not identical, processor 34 may be configured to compare the shapes of both waveforms and determine that the actual waveform 392 of the recent pump stroke corresponds to the shape of baseline waveform 390. In such a case, processor 34 may determine that actual waveform 392 corresponds to a normal pump stroke and that no fault condition exists. In another example, the actual waveform of each pump stroke is uploaded to another computing device, such as an external clinician programmer 20, so that the actual pump strokes may be analyzed further. The other computing device may store a history of the actual pump stroke waveforms so that a processor of the other computing device may analyze trends in the shape or other characteristics of the actual pump stroke waveforms to determine that a fault condition exists or to predict that a fault condition is likely to occur.

In one example, baseline waveforms 390, 394, 396, 402, 404, 406, 414, 416, 422, 426, 428, 430 are stored on the memory of another computing device, such as on external programmer 20, which may be a clinician programmer, and the waveform of each pump stroke are uploaded from IMD 12 to the other computing device so that a processor on the other computing device may be used to compare the shapes of the actual pump stroke to the shapes of baseline waveforms 390, 394, 396, 402, 404, 406, 414, 416, 422, 426, 428, 430 and determine if a particular actual waveform corresponds to a particular baseline waveform 390, 394, 396, 402, 404, 406, 414, 416, 422, 426, 428, 430 that corresponds to a particular fault condition.

At a later time, however, IMD 12 may determine that the most recent pump stroke has an actual waveform 398, shown in FIG. 14. Processor 34 may determine that actual waveform 398 corresponds to the shape of fully-stalled baseline waveform 394, even though actual waveform 398 and baseline waveform 394 are not identical. In such a case, processor 34 may determine that medical pump 40 has become fully stalled. Similarly, processor may be configured to determine at least one of the following: that an actual waveform 400 corresponds to the shape of partial-stall baseline waveform 396 (FIG. 14) to determine that medical pump 40 is partially stalled; that an actual waveform 408 corresponds to the shape of a first gas-accumulation baseline waveform 402 or that an actual waveform 410 corresponds to the shape of a second gas-accumulation baseline waveform 404 (FIG. 15) to determine that gas has accumulated within medical pump 40; that an actual waveform 412 corresponds to the shape of air-locked baseline waveform 406 (FIG. 15) to determine that medical pump 40 has become air locked; that an actual waveform 418 corresponds to the shape of high-energy baseline waveform 414 (FIG. 16) to determine that a high-energy fault condition exists within medical pump 40; that an actual waveform 420 corresponds to the shape of low-energy baseline waveform 416 (FIG. 16) to determine that a low-energy fault condition exists within medical pump 40; to determine that an actual waveform 424 corresponds to the shape of voltage-depleted baseline waveform 422 (FIG. 17) to determine that battery 86 of medical pump 40 has a depleted voltage; and that actual waveform 432 corresponds to the shape of first blocked-outlet baseline waveform 426, that actual waveform 434 corresponds to the shape of second blocked-outlet baseline waveform 428, or that actual waveform 436 corresponds to the shape of third blocked-outlet baseline waveform 430 (FIG. 18) to determine that the outlet of medical pump 40 is blocked.

In one example, processor 34 may compare a stored actual waveform corresponding to a pump stroke to a baseline waveform by performing comparison calculations to determine if the waveform and the baseline waveform are within a predetermined variance of one another. For example, processor 34 may perform a root-mean-square analysis of a recent actual waveform 392, 394, 398, 408, 410, 412, 418, 420, 424, 432, 434, 436 and each baseline waveform 390, 394, 396, 402, 404, 406, 414, 416, 422, 426, 428, and 430 stored in memory 36, wherein the recent actual waveform 392, 394, 398, 408, 410, 412, 418, 420, 424, 432, 434, 436 may be determined to correspond to a particular baseline waveform 390, 394, 396, 402, 404, 406, 414, 416, 422, 426, 428, or 430 when the root mean square between the two waveforms is within a certain predetermined threshold.

In another example, certain landmarks of the actual waveform 392, 394, 398, 408, 410, 412, 418, 420, 424, 432, 434, 436 may be compared to baseline waveforms 390, 394, 396, 402, 404, 406, 414, 416, 422, 426, 428, and 430 to determine if actual waveform 392, 394, 398, 408, 410, 412, 418, 420, 424, 432, 434, 436 indicates that a fault condition exists. For example, as shown in FIG. 6 and described above, the current value is less at an initial peak 136 of a partial-stall waveform 130 compared to the current at initial peak 116 of a normal waveform 110, nadir 140 of partial-stall waveform 130 occurs earlier than nadir 120 of normal waveform 110, and nadir 140 has a lower current value than nadir 120. Therefore, the current value of the initial peak, the time of the nadir, and/or the current value at the nadir of actual waveform 392 (FIG. 13) and actual waveform 400 (FIG. 14) may be compared to that of baseline waveforms 390, 396 to determine which actual waveform 392, 400 corresponds to a normal pump stroke and which corresponds to a partially stalled medical pump 40. As described above for various types of fault conditions, other landmarks on the current waveforms may be used to determine which baseline waveform a particular actual waveform may correspond. The landmark or landmarks that may be used to analyze actual waveforms include at least one of: a current rise rate of change prior to a initial peak, a current value at the initial peak, a time of the initial peak, a current value at the nadir, a time of the nadir, a change in current between the initial peak and the nadir, a change in time between the initial peak and the nadir, a width of a trough that forms nadir, the existence and type of an inflection point indicating an end of a stroke (e.g. a nadir or a flattening inflection point), a current value of a second peak, and a time at the second peak.

In another example, processor 34 may determine a number of comparison points at set times for actual waveform 392, 394, 398, 408, 410, 412, 418, 420, 424, 432, 434, 436 and for each baseline waveform 390, 394, 396, 402, 404, 406, 414, 416, 422, 426, 428, and 430, such as by determining the current value at set time points, for example, after every millisecond or every half of a millisecond. Then, processor 34 may determine the difference between the comparison point for actual waveform 392, 394, 398, 408, 410, 412, 418, 420, 424, 432, 434, 436 and each baseline waveforms 390, 394, 396, 402, 404, 406, 414, 416, 422, 426, 428, and 430 at each time point.

Processor 34 may determine that an actual waveform 392, 394, 398, 408, 410, 412, 418, 420, 424, 432, 434, 436 corresponds to a particular baseline waveform 90, 394, 396, 402, 404, 406, 414, 416, 422, 426, 428, 430 if a predetermined number of the comparison points from actual waveform 392, 394, 398, 408, 410, 412, 418, 420, 424, 432, 434, 436 are within a predetermined variance from the corresponding comparison points from a particular baseline waveform 90, 394, 396, 402, 404, 406, 414, 416, 422, 426, 428, 430. For example, processor 34 may determine comparison points for a particular actual waveform 392, 394, 398, 408, 410, 412, 418, 420, 424, 432, 434, 436 at 1 ms, 2 ms, 3 ms, 4, ms, 5 ms, 6 ms, 7 ms, 8 ms, 9 ms, and 10 ms for a total of ten comparison points that can be compared to comparison points for the same time points on baseline waveforms 90, 394, 396, 402, 404, 406, 414, 416, 422, 426, 428, and 430.

Processor 34 may be configured to determine how many comparison points from actual waveform 392, 394, 398, 408, 410, 412, 418, 420, 424, 432, 434, 436 are within a predetermined threshold, e.g., within about 0.01 amperes, from the corresponding comparison points from each baseline waveform 90, 394, 396, 402, 404, 406, 414, 416, 422, 426, 428, and 430 at the same comparison point time. Processor 34 may determine that actual waveform 434 corresponds to blocked-outlet baseline waveform 428, for example, when the number of comparison points that are within the predetermined threshold is equal to or greater than a certain number. For example, processor 34 may determine that actual waveform 392, 394, 398, 408, 410, 412, 418, 420, 424, 432, 434, 436 corresponds to a particular fault condition baseline waveform 90, 394, 396, 402, 404, 406, 414, 416, 422, 426, 428, and 430, and thus determine which particular fault condition exists, when at least 50%, or at least five of ten, of the comparison points are within the predetermined threshold. In another example, processor 34 may determine that the particular fault condition exists when at least 60%, or at least six of ten, of the comparison points are within the predetermined threshold. In another example, processor 34 may determine that the particular fault condition exists when at least 75%, or at least eight of ten, of the comparison points are within the predetermined threshold. In another example, processor 34 may determine that the particular fault condition exists when at least 80%, or at least eight of ten, of the comparison points are within the predetermined threshold. In another example, processor 34 may determine that the particular fault condition exists when at least 90%, or at least nine of ten, of the comparison points are within the predetermined threshold. Processor 34 may also be configured to determine that the particular fault condition exists only when 100%, or all ten of ten, of the comparison points are within the predetermined threshold.

In one example, any parameter that is used by processor 34, or by the processor of another computing device, to determine if a fault condition exists may be made configurable by a user via a programming device, such as external programmer 20, so that the parameter may be modified during the life of IMD 12. Examples of situations where the parameters may be modified or reconfigured include a change in the therapeutic agent being delivered, such as a change in composition or concentration of the therapeutic agent being delivered by pump 40. The parameter being changed may be changed, for example, by a user using external programmer 20 or another external computing device, such as a clinician, automatically by the processor of the external programmer, or automatically by processor 34 of IMD 12. Automatic changing of a parameter may occur, for example, based on factors such as battery life of power source 42 or the life of the pumping system over time, e.g. as the number of pump cycles increase over time. Parameters may also be customized to each specific pump 40 of each specific IMD 12 during manufacturing and programmed using a manufacturing programmer to memory 36 based on a manufacturing test, on pump type, on the intended use of the specific IMD 12, e.g., the specific therapy for which IMD 12 will be used or the specific therapeutic agent(s) that IMD 12 may be used to deliver, and other manufacturing parameters and configurations.

In another example, the energy that is actually passed through coil 50 in order to move actuator 52 through each pump stroke may be calculated, and the calculated energy may be used, either alone or in conjunction with the current waveform through coil 50 or with other characteristics of the pump stroke energy, to determine whether a fault condition exists. As described above, the amount of energy required to move actuator 52 through a normal pump stroke may be different than the amount of energy required for a pump stroke for various fault conditions. For example, partial-stall pump strokes, gas-accumulation pump strokes, and low-energy pump strokes tend to require less energy to complete the pump stroke compared to a normal pump stroke. Blocked-outlet pump strokes and high-energy pump strokes tend to require more energy to complete the pump stroke compared to a normal pump stroke. The energy that passes through coil 50 can be determined by several methods. In one example, IMD 12 includes a voltage sensor 102 that measures the voltage across coil 50. Although voltage sensor 102 is shown as measuring the voltage directly across coil 50, a voltage sensor may be placed across other portions of the circuit powering coil 50. For example, since the resistance of coil current sensor 100 and switching device 92 are each quite low, the voltage across capacitor 88 can be measured, such as with the capacitor voltage sensor 104 shown in FIG. 4, and the voltage across capacitor 88 can be assumed to be approximately equal to the voltage across coil 50.

In one example, processor 34 may determine whether a fault condition exists within medical pump 40 based on a set of pump strokes by determining how many of the plurality of pump strokes indicate that a particular fault condition exists. In one example, when a predetermined number of the set of pump strokes indicate a particular fault condition, processor 34 may determine that the particular fault condition does exist. For example, processor 34 may keep a moving window record of the most recent pump strokes, e.g., the last 10 pump strokes.

For example, if IMD 12 is programmed to deliver about 48 pump strokes per day, or about two pump strokes per hour, the number of pump strokes in the moving window set and the predetermined number may be set to be fairly low, e.g. a moving window of 4 pump strokes (about two hours of delivery) while the predetermined number may be 2 pump strokes (50% of the moving window), so that processor 34 can make a determination about a fault condition within about two hours of the genesis of the fault condition. However, if IMD 12 delivers at a faster rate, such as 480 pump strokes per day, or on average about every three minutes, the moving window and the predetermined number may be set to be larger, such as a moving window set of 10 pump strokes and a predetermined number of seven. In such a case, IMD 12 can be more confident that a particular fault condition exists (because 70%, rather than 50% of recent pump strokes indicated the existence of a fault condition), while still determining the existence of the fault condition in less time (e.g., after about 30 minutes rather than in about 2 hours). In one example, IMD 12 may be configured so that the parameters for determining whether a fault condition exists using a moving window set of recent pump strokes may be reprogrammed during the life of IMD 12, such as via telemetry through wireless communications link 22 between external programmer 20 and IMD 12. For example, processor 34 may be reconfigured to change the number of pump strokes that will make up the moving window set and/or the predetermined number of pump strokes (or percentage of pump strokes) within the moving window that will trigger a finding that a fault condition exists. In one example, the total number of pump strokes that will be included in the moving window set may be programmable over a large range, e.g., between 1 stroke and 256 strokes, and the predetermined number of pump strokes that will be necessary to trigger a finding that a default condition exists may also be programmable over a large ranger, for example between 1 and whatever value of the moving window set is selected. For example, processor 34 may be programmed, such as by a user, for example a clinician, so that the moving window set includes the most recent X pump strokes, where X is an integer between 1 and 256, and that the predetermined number of pump strokes that will trigger a finding of a fault condition will be Y pump strokes, wherein Y is between 1 and X. Processor 34 may be configured to determine that a fault condition exists if at least Y out of the most recent X pump strokes indicates that a fault condition exists. However, if at a later time, processor 34 or a user determines that the current configuration (e.g., moving window set of X, predetermined number of pump strokes Y), is not providing adequate findings regarding the existence of fault conditions, processor 34 may be reprogrammed to change the moving window set to another value N, and/or processor 34 may be programmed to change the predetermined number to another value M, such that a fault condition may be determined to exist, for example, if at least M out of the most recent N pump strokes (or M out of the most recent X, or Y out of the most recent N) indicates that a fault condition exists.

In one example, processor 34 may determine that several recent pump strokes have current waveforms that correspond to the shape of a blocked-outlet waveform 310, 330, 350 (FIG. 11.) When a predetermined number of the set of most recent pump strokes have a waveform shape that corresponds to the blocked-outlet waveform shape 310, 330, 350, then processor 34 may determine that the outlet medical pump 40 is blocked. In one example, processor 34 may determine that medical pump 40 is blocked when at least about 50%, e.g., five of the ten, of the recent pump strokes correspond to a blocked-outlet waveform shape 310, 330, 350. In another example, processor 34 may determined that medical pump 40 is blocked when at least about 60%, e.g., six out of ten, of the pump strokes correspond to a blocked-outlet waveform shape 310, 330, 350, such as at least about 75%, e.g., eight out of ten, for example, at least about 80%, e.g., eight out of ten, and in one example at least about 90%, e.g., nine out of ten, of the pump strokes correspond to a blocked-outlet waveform shape 310, 330, 350. In one example, processor 34 may only determine that medical pump 40 is blocked when 100% of the plurality of recent pump strokes, e.g., all ten out of ten, correspond to a blocked-outlet waveform shape 310, 330, 350. If fewer than the predetermined number or percentage of pump strokes correspond to a blocked-outlet waveform shape 310, 330, 350, then processor 34 may determine that pump 40 is not blocked. Similar analysis may be performed comparing a set of recent pump strokes to each of the other types of fault conditions. In one example, IMD 12 may be configured so that the number of consecutive pump strokes required to trigger a finding of a fault condition may be reprogrammed during the life of IMD 12, such as by reconfiguring processor 34 to change the predetermined number of consecutive pump strokes required.

The predetermined number of pump strokes and the number of pump strokes to be included in the set that are used by processor 34 to determine if a fault condition exists may depend on the therapy rate being delivered by IMD 12, e.g., the predetermined number and the set may depend on the rate of pump strokes delivered by IMD 12 over time, as well as the under-infusion risks and side effects associated with the therapeutic agent being delivered.

In another example, processor 34 may determine that a particular fault condition exists when a predetermined number of consecutive pump strokes correspond to the particular fault condition, such as by having a current waveform shape that corresponds to the expected waveform shape for the particular fault condition. The predetermined number of consecutive pump strokes that will cause processor 34 to determine that the fault condition exists may depend on the therapy rate being delivered by IMD 12, the type of fault condition, and the under-infusion risks and side effects associated with the therapeutic agent being delivered. In one example, processor may determine that a particular fault condition exists when at least 3 consecutive pump strokes correspond to the particular fault condition, such as at least 5 consecutive pump strokes, for example at least 10 consecutive pump strokes. If fewer than the predetermined number of pump strokes correspond to the particular fault condition, then processor 34 may determine that the fault condition does not exist.

In one example, processor 34 may be configured to monitor a fault condition and determine if the fault condition becomes resolved over time, either on their own or through the application of a recovery action. For example, if processor 34 determines that pump 40 has become stalled, such as a full stall that corresponds to current waveform 126 (FIG. 5), processor 34 may be configured to check over time, such as after a predetermined number of pump strokes or attempted pump strokes, to see if the stall still exists. The method by which processor 34 may determine that a fault condition has resolved may be similar to the methods described above for determining if the fault condition exists in the first place.

For example, processor 34 may be configured to determine that a fault condition has been resolved based on a set of pump strokes by determining how many of the plurality of pump strokes indicate that the previously-detected fault condition no longer exists. In one example, processor 34 may keep a moving window record of the most recent pump strokes, e.g., the last 10 pump strokes, and determine that the particular fault condition no longer exists when a predetermined number of the moving window set correspond to a normal pump stroke, such as by having a shape that corresponds to normal baseline waveform 390. The predetermined number of pump strokes and the number of pump strokes to be included in the moving window may depend on the therapy rate being delivered by IMD 12, e.g., the predetermined number of pump strokes and the number of pump strokes to be included in the moving window may depend on the rate of pump strokes delivered by IMD 12 over time, as well as the under-infusion risks and side effects associated with the therapeutic agent being delivered. In one example, if IMD 12 is programmed to deliver about 48 pump strokes per day, or about two pump strokes per hour, the number of pump strokes in the moving window set and the predetermined number may be set to be fairly low, e.g. a moving window of 4 pump strokes (about two hours of delivery) while the predetermined number may be 2 pump strokes (50% of the moving window), so that processor 34 can determine that a fault condition has been resolved within about two hours of its resolution. However, if IMD 12 delivers at a faster rate, such as 480 pump strokes per day, or on average about every three minutes, the moving window and the predetermined number may be set to be larger, such as a moving window set of 10 pump strokes and a predetermined number of seven. In such a case, IMD 12 can be more confident that a particular fault condition has been resolved (because 70%, rather than 50% of recent pump strokes indicated resolution of the fault condition), while still determining the resolution of the existence of the fault condition in less time (e.g., after about 30 minutes rather than in about 2 hours). In one example, IMD 12 may be configured so that the parameters of determining whether a fault condition has been resolved using a moving window set of recent pump strokes may be reprogrammed during the life of IMD 12. For example, processor 34 may be reconfigured to change the number of pump strokes that will make up the moving window set and/or the predetermined number of pump strokes (or percentage of pump strokes) within the moving window that will trigger a finding that the fault condition has been resolved.

In one example, after determining that a blocked-outlet fault condition exists, such as by determining that several recent pump strokes have current waveforms that correspond to the shape of a blocked-outlet waveform 310, 330, 350 (FIG. 11), processor 34 may determine that the blocked outlet fault condition has been resolved when a predetermined number of the moving window set of most recent pump strokes have a waveform shape that corresponds to a normal waveform shape 110 rather than a blocked-outlet waveform shape 310, 330, 350. In such a case, processor 34 may determine that the previously existing blocked outlet fault condition has been resolved. In one example, processor 34 may determine that pump 40 is no longer blocked when at least about 50%, e.g., five of the ten, of the recent pump strokes correspond to a normal waveform shape 110. In another example, processor 34 may determined that pump 40 is no longer blocked when at least about 60%, e.g., six out of ten, of the pump strokes correspond to a normal waveform shape 110, such as at least about 75%, e.g., eight out of ten, for example, at least about 80%, e.g., eight out of ten, and in one example at least about 90%, e.g., nine out of ten, of the pump strokes correspond to a normal waveform shape 110. In one example, processor 34 may only determine that medical pump 40 is no longer blocked when 100% of the plurality of recent pump strokes, e.g., all ten out of ten, correspond to a normal waveform shape 110. If fewer than the predetermined number or percentage of pump strokes correspond to a normal waveform shape 110, then processor 34 may determine that the blocked-outlet fault condition still exists within pump 40.

In another example, processor 34 may only determine that a fault condition has been resolved if fewer than a predetermined number of the moving window set of recent pump strokes indicate that the previously-determined fault condition still exists. Continuing with the blocked-outlet example, processor 34 may, in addition to requiring that a predetermined number of pump strokes within the moving window correspond to a normal waveform shape 110, require that fewer than a predetermined number of pump strokes within the moving window correspond to a blocked-outlet waveform shape 310, 330, 350. In one example, processor 34 may determine that pump 40 is no longer blocked only when fewer than 50%, e.g., less than five of the ten, of the recent pump strokes correspond to a blocked-outlet waveform shape 310, 330, 350. In another example, processor 34 may determined that pump 40 is no longer blocked only when fewer than about 40%, e.g., less than four out of ten, of the pump strokes correspond to a blocked-outlet waveform shape 310, 330, 350, such as less than about 25%, e.g., two out of ten, for example, less than at least about 20%, e.g., two out of ten, and in one example at least about 15%, e.g., one out of ten, of the pump strokes correspond to a blocked-outlet waveform shape 310, 330, 350. In one example, processor 34 may only determine that medical pump 40 is no longer blocked when 0% of the plurality of recent pump strokes, e.g., none of the ten, correspond to a blocked-outlet waveform shape 310, 330, 350. If more than the predetermined number or percentage of pump strokes correspond to a blocked-outlet waveform shape 310, 330, 350, then processor 34 may determine that the blocked-outlet fault condition still exists within pump 40, even if the requirement of the number or percentage of normal pump strokes is met. Similar analysis may be performed comparing a set of recent pump strokes to each of the other types of fault conditions.

In another example, processor 34 may determine that a particular fault condition has been resolved when a predetermined number of consecutive pump strokes correspond to a normal pump stroke, such as by having a current waveform shape that corresponds to the expected waveform shape for a normal waveform. The predetermined number of consecutive pump strokes that will cause processor 34 to determine that the fault condition has been resolved may depend on the therapy rate being delivered by IMD 12, the type of fault condition, and the under-infusion risks and side effects associated with the therapeutic agent being delivered. In one example, processor may determine that a particular fault condition has been resolved when at least 3 consecutive pump strokes correspond to a normal pump stroke, such as at least 5 consecutive pump strokes, for example at least 10 consecutive pump strokes. If fewer than the predetermined number of consecutive pump strokes indicate that the fault condition has been resolved, then processor 34 may determine that the fault condition still exists. In one example, IMD 12 may be configured so that the number of consecutive pump strokes required to trigger a finding that the fault condition has been resolved may be reprogrammed during the life of IMD 12, such as by reconfiguring processor 34 to change the predetermined number of consecutive pump strokes required.

Returning to FIG. 2, IMD 12 may comprise an alarm component 438 that is configured to produce an alarm in various situations in order to alert a patient or other user, such as when an error within IMD 12 requires a decision by the patient or a clinician treating the patient. In one example, alarm component 438 is a piezoelectric alarm device 440 (FIG. 3) that is configured to produce an audible alarm when a voltage is applied to a piezoelectric material by an alarm drive circuit. In another example, alarm component 438 may comprise a vibrational alarm that is felt by the patient. Alarm component 438 may also comprise a signal sent by IMD 12 to another device, such as an external computing device, for example programmer 20, in order to draw a user's attention, such as an audible, visual, textual, or other type of alert that is perceived by a user, such as the patient or a clinician. For example, alarm component 438 may initiate a signal that is sent to external programmer 20 that is used by patient, causing external programmer 20 to produce an alarm, such as an audio alarm or a visual alarm displayed on external programmer.

In one example, alarm component 438 may be configured to initiate an alarm when processor 34 determines that a fault condition exists within medical pump 40. IMD 12 may be configured so that for certain fault conditions, alarm component 438 may initiate a one-time alarm or a repeating alarm that ceases on its own. IMD 12 may also be configured so that for some other fault conditions, alarm component 438 may initiate an alarm that must be acknowledged by the patient, such as an audible and visual alarm that must be cleared by the patient, and which may also include an informational notice to a clinician. IMD 12 may also be configured such that for other fault conditions, alarm component 438 initiates an alarm that requires acknowledgement by a clinician, such as a visual alarm that is displayed on an external computing device monitored by the clinician. If processor 34 is configured to determine whether a particular fault condition has been resolved, then processor 34 may also be configured to automatically remove any alarms that may have been initiated as a result of the detection of a fault condition. For example, if processor 34 is configured to activate piezoelectric alarm device 440 when a fault condition is detected, then processor 34 may also be configured to deactivate piezoelectric alarm device 440 when it is determined that the same fault condition has been resolved. Processor 34 may also be configured to log a time stamp at the time a fault condition is detected and at the time the fault condition is determined to be resolved. Processor 34 may also log other relevant data that can be used by processor 34, another computing device, such as external programmer 20, and/or by a user, such as a clinician. Other relevant data that may be logged by processor 34 may include the basis for determining that a fault condition exists, the basis for determining that a fault condition was resolved, and, if applicable, any recovery actions that were attempted to resolve the fault condition and if the recovery action was successful or not.

In one example, IMD 12 may also be configured to perform a recovery action in response to the detection of a fault condition in order to attempt to remove or remedy the detected fault condition. The nature of the recovery action may depend on the specific detected fault condition. Each specific fault condition may have its own recovery action. A fault condition may also have more than one recovery action that can be initiated. A particular recovery action for a specific fault condition may comprise processor 34 initiating a recovery sequence, wherein the recovery sequence comprises a series of actions by one or more components within IMD 12.

In one example, wherein processor 34 determines that there is gas accumulation within medical pump 40, a recovery action may comprise delivering a bolus of fluid through medical pump 40 in an attempt to dislodge or force through the accumulated gas. Delivery of a bolus of fluid may also be used as a potential recovery action for a blocked outlet of medical pump 40 in an attempt to dislodge or unblock whatever may be obscuring the outlet of medical pump 40, or for a partial stall fault condition or a short or reduced pump stroke length fault condition. Other recovery actions that may be taken by IMD 12 may include increasing the coil drive voltage or increasing the charge time of capacitor 88, such as to increase the initial energy through coil to drive actuator 52 if it is stalled, decreasing the charge time of capacitor 88, such as to decrease the time between pump strokes, increasing the stroke duration, such as to increase the total energy that may be supplied over the entire pump stroke to attempt to drive actuator 52 if it is stalled, increasing the stroke rate, e.g., the number of strokes per minute, such as to push accumulated air through pump 40 or to move particulates or other foreign material through pump 40. A recovery action for IMD 12 may also include initiating a pump reset, for example in response to a software error fault condition in the digital logic which may disrupt the state machine or waveform shape fault condition or reinitializing IMD 12. A pump reset may be used as a recovery action for other fault conditions described herein, including any stall-related fault condition, when the fault condition is possibly related to an error within the electro-mechanical system that may be resolved by a reset. For example, in a stall condition, the driver electronic logic for the electro-magnetic system may be stuck, a sensor within IMD 12 is sensing incorrectly, software running on processor 34 and managing the operation of pump 40 and/or other activities within pump 40, including determining the existence of fault conditions, may have an unknown error state, all of which may be resolved with a reset.

A recovery action may also comprise placing medical pump 40 into a reduced delivery mode that continues to deliver the therapeutic fluid to the patient, but at a reduced rate so that the patient will continue to receive a minimum therapeutic amount of the therapeutic agent after a fault condition is determined to exist. The reduced delivery mode, also referred to as a "limp mode," may allow the patient to receive some of the therapeutic agent, such as to prevent withdrawal symptoms, for a period of time that is sufficient for the patient to return to a clinic or clinician to either remedy the fault condition or replace the medical pump 40, if necessary.

As described above, processor 34 may be configured to determine whether a particular fault condition has been resolved. In one example, if IMD 12 is configured to perform a recovery action, processor 34 may also be configured to determine whether the recovery action resolved the fault condition. The methods by which processor 34 may determine if the recovery action resolved the particular fault condition are the same as the methods described above regarding determining if a fault condition has been resolved, e.g., whether a predetermined number or percentage of a moving window set indicate that the fault condition has been resolved, or whether a predetermined number of consecutive pump strokes indicate that the fault condition has been resolved. If processor 34 determines that the fault condition has been resolved after a recovery action was initiated, it may be assumed that the recovery action resolved the fault condition. A log of all recovery actions attempted may be stored, such as in memory 36 or firmware of IMD 12 or within a memory of another computing device, such as external programmer 20. The log of recovery actions may include the type of recovery action attempted, the time the recovery action was attempted, the method used for determining if the recovery action was successful in resolving the fault condition, and the time at which the determination of whether the fault condition was resolved was made.

Figure 19:
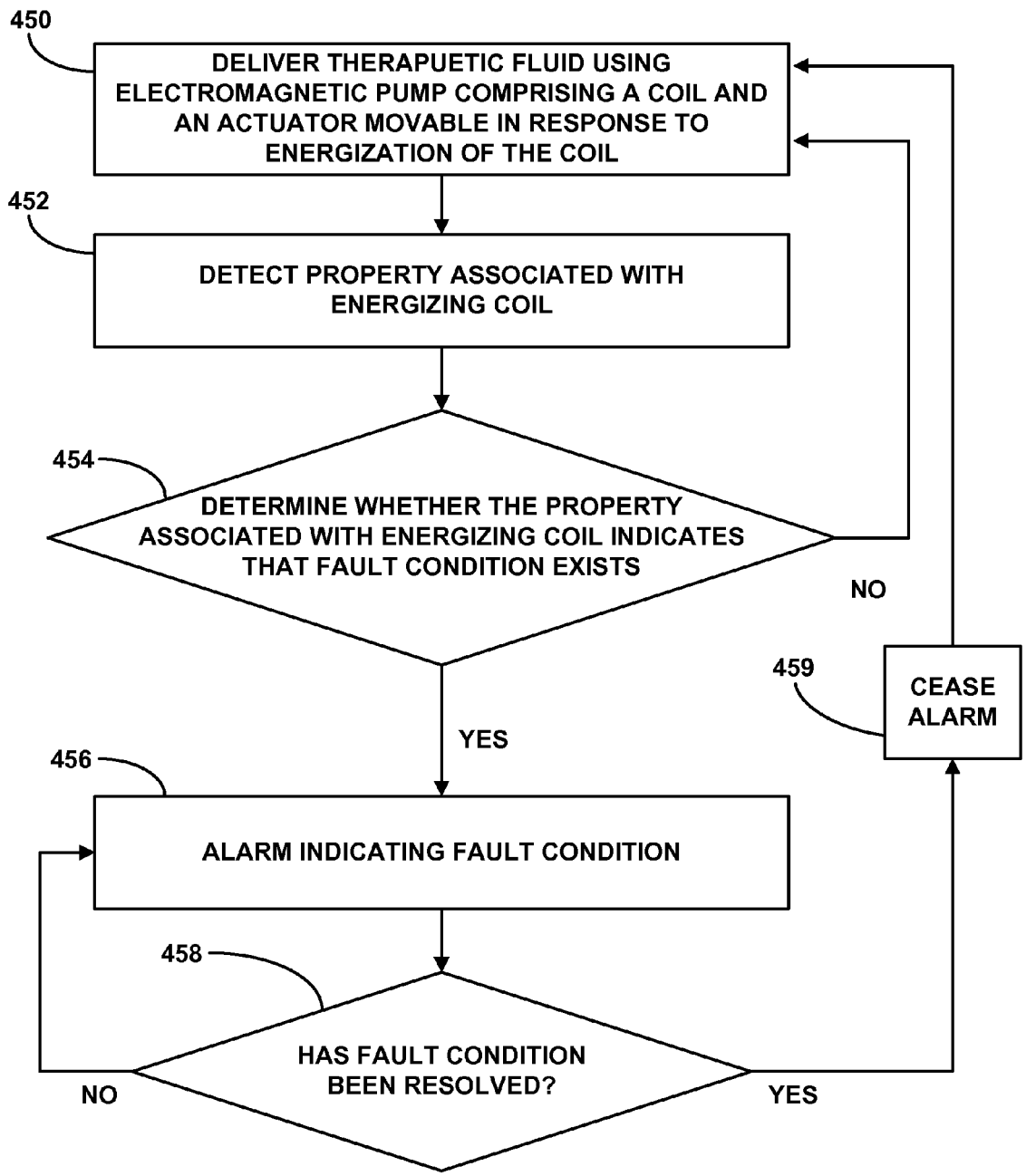
FIG. 19 is a flow diagram illustrating an example method for determining whether a fault condition exists within a medical pump.

FIG. 19 is a flow diagram showing an example method of determining if a fault condition exists within medical pump 40. The example method includes delivering therapeutic fluid using a medical pump 40 (450), wherein pump 40 comprises an actuation mechanism configured to be energized to provide a pump stroke, such as a coil 50 and an actuator 52 that is movable in response to energization of coil 50. Next, a property associated with the energy required to energize coil 50 is detected (452). Next, it is determined whether the property associated with the energy required to energize coil 50 indicates that a fault condition exists with medical pump 40 (454). As described above, the property associated with the energy required to energize coil 50 may comprise one of the shape of a current waveform through coil 50 when providing, or attempting to provide, for a pump stroke when a fault condition exists, a energy supplied to coil 50 in order to produce or attempt to produce a pump stroke when the fault condition exists, and a voltage across coil 50 when providing or attempting to provide a pump stroke. In one example, determining that a fault condition exists may include logging a time stamp, such as by storing the time stamp in memory 36, to indicate the time at which the fault condition was first detected.

Detecting the property associated with energizing the actuation mechanism (452) may be performed by a sensor, such as coil current sensor 100, voltage current sensor 102, or capacitor sensor 104 described above. Determining whether the property associated with energizing the actuation mechanism indicates that a fault condition exists (454) may be performed by a processor that analyzes the output from the sensor. In one example, processor 34 of IMD 12 may be configured to analyze the output of the sensor and determine if the property associated with energizing the actuation mechanism indicates the existence of a fault condition. In another example, a processor of another computing device, such as a processor of external programmer 20, may determine if the property associated with energizing the actuation mechanism indicates that a fault condition exists.

As described in more detail elsewhere in this disclosure, determining that the property associated with energizing the actuation mechanism indicates that a fault condition exists (454) may include determining that the property associated with energization of coil 50 is within a certain threshold of a value or characteristic of the property associated with energization of coil 50 that is expected when a particular fault condition exists. Other methods may be used to indicate that a particular fault condition exists, including anything with respect to the property associated with energization of coil 50 that is connected to, related to, demonstrates, suggests, signifies, specifies, or is a sign that the particular fault condition exists.

After it is determined that a fault condition exists, processor 34 may initiate an alarm (456), which may include some form of alarm that is intended to get the user's attention, such as an audible alarm, as well as a notification of the type of fault condition detected. In one example, initiating the alarm (456) may comprise activating an alarm component 438, such as activating the alarm drive circuit of an audible alarm, for example a piezoelectric alarm 440, in order to produce an audible alarm sound that is heard by the patient. The alarm may also comprise a vibrational alarm that is felt by the patient, or a signal sent by IMD 12 to another device, such as an external computing device, for example programmer 20, in order to draw a user's attention, such as an audible, visual, textual, or other type of alert that is perceived by a user, such as the patient or a clinician. In one example, alarming (456) may comprise activating the alarm component 438 at periodic intervals, e.g., initiating an alert every 15 minutes, until the fault condition is resolved.

Once it is determined that a fault condition does exist within pump 40 (454) and after an alarm has been activated (456), at a later time the method may include monitoring medical pump 40 and determining if the fault condition has been resolved (458). For example, processor 34 may be configured to wait a predetermined period of time or a predetermined number of pump strokes and then determine if the fault condition has been resolved. The monitoring of medical pump 40 to determine if the fault condition has been resolved (458) may also be performed by the processor of another computing device, such as external programmer 20. As described in more detail elsewhere in this disclosure, determining that a fault condition has been resolved (458) may include determining that the property associated with energization of coil 50 is within a certain threshold of a value or characteristic of the property associated with energization of coil 50 that is expected when a fault condition does not exist. Other methods may be used to indicate that a particular fault condition exists, including anything with respect to the property associated with energization of coil 50 that is connected to, related to, demonstrates, suggests, signifies, specifies, or is a sign that the particular fault condition exists. If the fault condition is resolved, then processor 34 may cause the alarm to cease (459) and IMD 12 may continue to deliver fluid using the actuation mechanism of the medical pump 40 (450). If the fault condition is not resolved, than the alarm may be continued, or if the alarm is a periodic alarm, it may be reinitiated (456), to indicate to the patient or another user that the fault condition still exists. In one example, monitoring of medical pump 40 to determine if the fault condition has been resolved (458) may be performed on a periodic basis, e.g. every 5 minutes, every 15 minutes, every 30 minutes, every hour, etc. If the monitoring of medical pump 40 (458) is repeated on a periodic basis, a reinitiation/reactivation of an alarm (456) that is performed after it is determined that the fault condition still exists may be performed at the same periodic basis or at a different periodic basis. In one example, monitoring of medical pump 40 (458) may be performed more frequently than reinitiation/reactivation of an alarm (456), such as monitoring of medical pump 40 (458) being performed every 15 minutes, while reinitiating/reactivating alarm (456) may be performed every hour if the fault condition is not resolved. In another example reinitiation/reactivation of an alarm (456) may be performed each time that monitoring of medical pump 40 (458) determines that the fault condition still exists.

Figure 20:
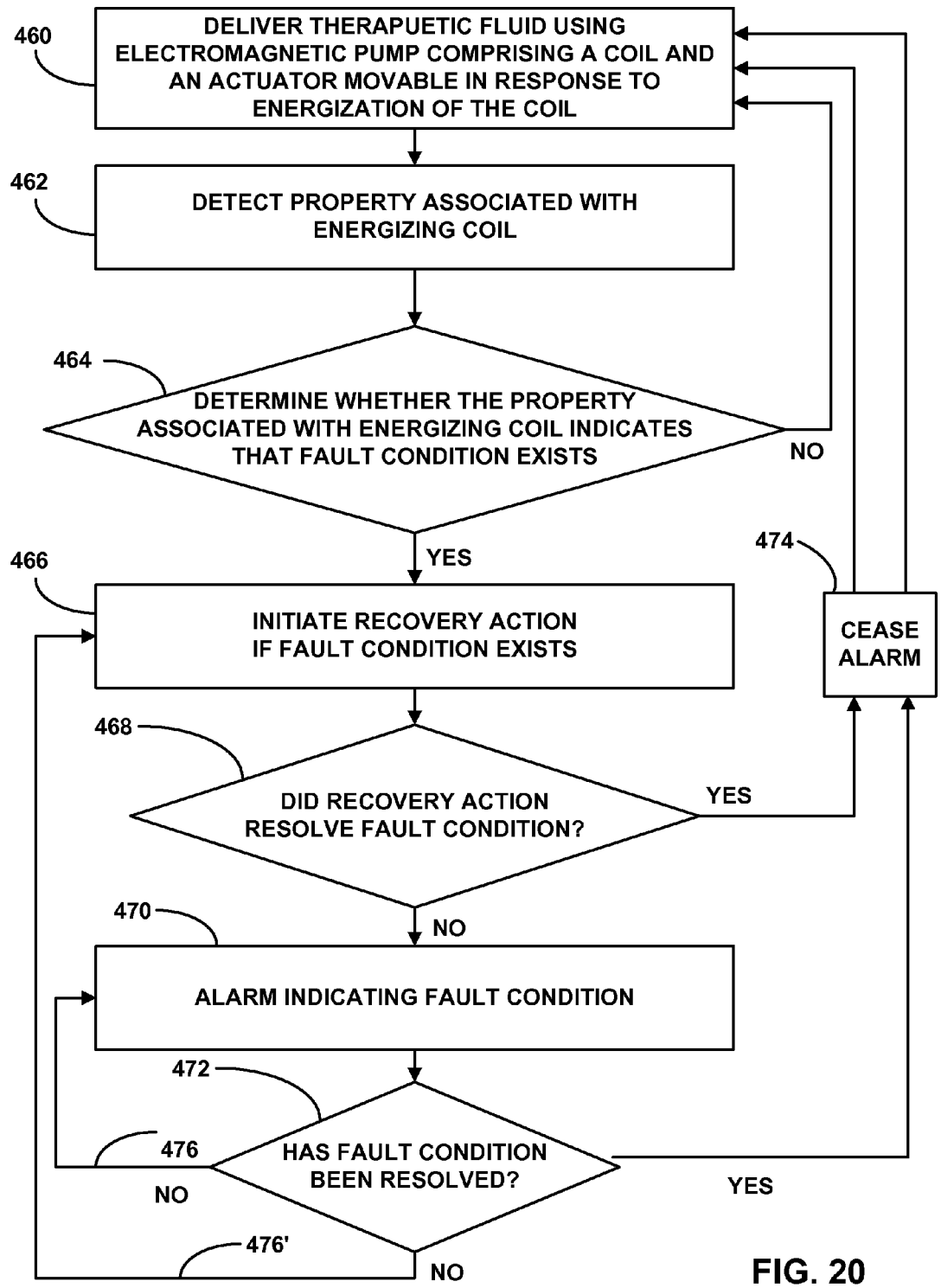
FIG. 20 is a flow diagram illustrating another example method for determining whether a fault condition exists within a medical pump.

FIG. 20 is a flow diagram showing another example method of determining if a fault condition exists within medical pump 40. The example method of FIG. 20 is similar to the method of FIG. 19, and may be considered a specific example of the method of FIG. 19. The example method of FIG. 20 includes delivering therapeutic fluid using a medical pump 40 (460), wherein pump 40 comprises an actuation mechanism configured to be energized to provide a pump stroke, such as a coil 50 and an actuator 52 that is movable in response to energization of coil 50. Next, a property associated with the energy required to energize coil 50 is detected (462). Finally, it is determined whether the property associated with the energy required to energize coil 50 indicates that a fault condition exists with medical pump 40 (464). As described above, the property associated with the energy required to energize coil 50 may comprise one of the shape of a current waveform through coil 50 when providing, or attempting to provide, for a pump stroke when a fault condition exists, a energy supplied to coil 50 in order to produce or attempt to produce a pump stroke when the fault condition exists, and a voltage across coil 50 when providing or attempting to provide a pump stroke. In one example, steps (460), (462), and (464) are substantially similar to method steps (450), (452), and (454) described above.

The method of FIG. 20 may also include initiating a recovery action (466) when it is determined that the property associated with the energization of coil 50 indicates that a fault condition exists. As described above, the recovery action initiated may be specific to the particular type of fault condition detected, such as delivery of a bolus of fluid when a gas-accumulation fault condition or blocked-outlet fault condition is detected. Initiating a recovery action (466) may comprise processor 34 initiating a recovery sequence or one or more actions that are performed by components of IMD 12 or by external devices, such as external programmer 20. The method may also include initiating an alarm when a fault condition is detected at or near the same time that a recovery action is initiated in order to notify a user, such as the patient or a clinician, of the existence of the fault condition.

The method of FIG. 20 may also include determining if the recovery action resolved the detected fault condition (468). Determining if the recovery action resolved the fault condition (468) may include performing an additional pump stroke, or series of pump strokes, and analyzing the additional pump stroke or strokes to determine if the fault condition still exists, such as by performing any of the methods of analysis described above for detecting a fault condition in the first place. Other methods may be used to indicate that a particular fault condition has been resolved, including anything with respect to the property associated with energization of coil 50 that is connected to, related to, demonstrates, suggests, signifies, specifies, or is a sign that the particular fault has been resolved. If the fault condition is resolved, then IMD 12 may continue to deliver fluid using the actuation mechanism of the medical pump 40 (450). If the fault condition is resolved, then IMD 12 may also automatically clear any alarms that may have been initiated upon detection of the fault condition (474).

If the fault condition is not resolved, than an alarm may be initiated (470) that indicates that a recovery action was unsuccessful. In one method, IMD 12 may be configured to only initiate an alarm after it has been determined that a recovery action was unsuccessful in resolving a fault condition (470). In another example, IMD 12 may be configured to initiate an alarm both if and when the fault condition is detected, e.g., at or around the time that a recovery action is initiated (466), and also if and when a recovery action fails to resolve the fault condition (470). Whether one or both alarms are initiated may depend on the specific type of fault condition. If the fault condition was not resolved by a first attempt at a recovery action, the recovery action may be repeated one or more times to attempt to resolve the fault condition, or a second, different recovery action may be attempted. The alarm that is initiated (470) may include some form of alarm that is intended to get the user's attention, such as an audible alarm, as well as a notification of the type of fault condition detected. In one example, initiating the alarm (470) may comprise activating an alarm component 438, such as activating the alarm drive circuit of an audible alarm, for example a piezoelectric alarm 440, in order to produce an audible alarm sound that is heard by the patient. The alarm may also comprise a vibrational alarm that is felt by the patient, or a signal sent by IMD 12 to another device, such as an external computing device, for example programmer 20, in order to draw a user's attention, such as an audible, visual, textual, or other type of alert that is perceived by a user, such as the patient or a clinician. In one example, alarming (470) may comprise activating the alarm component 438 at periodic intervals, e.g., initiating an alert every 15 minutes, until the fault condition is resolved.

If it is determined that the recovery action did not resolve the fault condition and after an alarm has been activated (470), at a later time the method of claim 20 may include monitoring medical pump 40 and determining if the fault condition has been resolved (472). Monitoring of pump 40 (470) may be similar to the monitoring of pump 40 (458) described above with respect to FIG. 19. For example, processor 34 may be configured to wait a predetermined period of time or a predetermined number of pump strokes after alarming (470) and then determine if the fault condition has been resolved. The monitoring of medical pump 40 to determine if the fault condition has been resolved (470) may also be performed by the processor of another computing device, such as external programmer 20. As described in more detail elsewhere in this disclosure, determining that a fault condition has been resolved (470) may include determining that the property associated with energization of coil 50 is within a certain threshold of a value or characteristic of the property associated with energization of coil 50 that is expected when a fault condition does not exist. Other methods may be used to indicate that a particular fault condition exists, including anything with respect to the property associated with energization of coil 50 that is connected to, related to, demonstrates, suggests, signifies, specifies, or is a sign that the particular fault condition exists. If the fault condition is resolved, then processor 34 may cause the alarm to cease (474) and IMD 12 may continue to deliver fluid using the actuation mechanism of the medical pump 40 (450) and may also clear any alarms that may have been initiated upon detection of the fault condition.

In one example, if the fault condition is not resolved, than the method may take one or both of the following actions: (a) the alarm may be continued, or if the alarm is a periodic alarm, it may be reinitiated or reactivated, as indicated by (476), in order to alert the patient or another user that the fault condition still exists; or (b) processor 34 may initiated another recovery action (466), as indicated by (476'). The recovery action performed after (476') may be the same recovery action performed in the first instance of performing a recovery action (466), or it may be a different recovery action. After a recovery action is initiated again (476', 466), the method may include once again determining if the recovery action resolved the detected fault condition (468). If the subsequent recovery action (476', 466) did resolve the fault condition, then IMD 12 may continue to deliver fluid using the actuation mechanism of the medical pump 40 (450) and any alarms that may have been initiated may be automatically cleared. If the subsequent recovery action (476', 466) did not resolve the fault condition, then the process of alarming (470) and monitoring pump 40 to determine if the fault condition has been resolved (472) may be repeated.

Although the target therapy delivery site described with reference to the foregoing examples is proximate to the spinal cord of a patient, other applications of therapy systems in accordance with this disclosure include alternative delivery sites. In some examples, the target delivery site may be proximate to different types of tissues including, e.g., nerves, e.g. sacral, pudendal or perineal nerves, organs, muscles or muscle groups. In one example, a catheter may be positioned to deliver a therapeutic fluid to a deep brain site or within the heart or blood vessels.

Delivery of a therapeutic fluid within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. A catheter may also be positioned to deliver insulin to a patient with diabetes. In other examples, the system may deliver a therapeutic fluid to various sites within a patient to facilitate other therapies and to manage other conditions including peripheral neuropathy or postoperative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

The techniques described in this disclosure, including those attributed to processor 34 of IMD 12 and external programmer 20 may be implemented, at least in part, in hardware, software, firmware or any combination thereof. For example, various aspects of the techniques may be implemented within one or more processors, including one or more microprocessors, digital signal processors (DSPs), application-specific integrated circuits (ASICs), field-programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

This disclosure refers to illustrative examples that are not meant to be construed in a limiting sense. Various modifications of the illustrative examples, as well as additional examples of the disclosure, will be apparent to persons skilled in the art upon reference to this description. Any specific numerical value or range described in the foregoing disclosure shall not be limiting, except for values or ranges included in the following claims.

The invention claimed is:

1. A medical device system comprising:
    a medical pump configured to deliver a therapeutic fluid to a patient, the medical pump comprising an actuation mechanism configured to be energized to provide a pump stroke;
    a sensor configured to detect a property associated with energizing the actuation mechanism, the property associated with energizing the actuation mechanism comprising a shape of at least a waveform portion of an electrical waveform applied to the actuation mechanism when the actuation mechanism is energized to provide the pump stroke; and
    a processor configured to:
        store a baseline shape that indicates one of a normal pump stroke and a fault condition in a memory,
        compare the baseline shape to the shape of at least the waveform portion of the electrical waveform applied to the actuation mechanism when the actuation mechanism is energized to provide the pump stroke, and
        determine, based on the comparison, whether the shape of at least the waveform portion of the electrical waveform indicates that a fault condition exists within the medical pump.

2. The system of claim 1, wherein the processor is further configured to initiate a recovery action to attempt to remedy the fault condition if the processor determines that the shape of at least the waveform portion of the electrical waveform indicates that the fault condition exists.

3. The system of claim 2, wherein the recovery action comprises a recovery sequence initiated by the processor.

4. The system of claim 2, wherein the recovery action comprises at least one of:
    delivering a bolus of fluid through the medical pump;
    increasing a drive voltage of the actuation mechanism;
    increasing or decreasing a charge time of a capacitor that drives the actuation mechanism;
    increasing a rate of pump strokes delivered by the medical pump;
    initiating a pump reset; and
    reinitializing the medical pump.

5. The system of claim 2, wherein the processor is further configured to determine whether the recovery action resolved the fault condition after initiating the recovery action.

6. The system of claim 1, wherein the processor is configured to monitor the medical pump to determine whether the fault condition has been resolved if the processor determines that the shape of at least the waveform portion of the electrical waveform indicates that the fault condition exists.

7. The system of claim 6, wherein the processor is configured to determine that the fault condition has been resolved when the processor determines that the shape of at least the waveform portion of the electrical waveform of each of a predetermined number of a set of prior pump strokes indicates that the fault condition has been resolved, or when the processor determines that the shape of at least the waveform portion of the electrical waveform of each of a predetermined number of consecutive pump strokes indicates that the fault condition has been resolved.

8. The system of claim 6, wherein the processor is configured to log a time stamp indicating a time at which the fault condition was determined to have been resolved if the processor determines that the fault condition has been resolved.

9. The system of claim 6, wherein the processor is configured to initiate an alarm when the processor determines that the shape of at least the waveform portion of the electrical waveform indicates that the fault condition exists and to clear the alarm when if the processor determines that the fault condition has been resolved.

10. The system of claim 1, wherein the shape of at least the waveform portion of the electrical waveform applied to the actuation mechanism when the actuation mechanism is energized to provide the pump stroke is a first shape of at least a first waveform portion of a first electrical waveform applied to the actuation mechanism when the actuation mechanism is energized to provide a first pump stroke, and wherein:

the sensor is configured to detect a second shape of at least a second waveform portion of a second electrical waveform applied to the actuation mechanism when the actuation mechanism is energized to provide a second pump stroke subsequent to the first pump stroke, the second shape being different than the first shape, the processor is configured to recognize a progression from the first shape of the at least first waveform portion to the second shape of the at least second waveform portion; and the processor is configured to determine, according to the progression from the first shape to the second shape, that the fault condition exists within the medical pump.

11. The system of claim 10, wherein the processor is configured to determine that the fault condition exists by determining that the progression from the first shape of the at least first waveform portion to the second shape of the at least second waveform portion occurs within a predetermined number of pump strokes.

12. The system of claim 1, wherein the actuation mechanism comprises a coil configured to be energized to provide a pump stroke and an actuator that is movable in response to the energization of the coil.

13. The system of claim 1, wherein the fault condition comprises one of a plurality of fault condition types, and wherein the processor is further configured to identify which of the plurality of fault condition types exists if the processor determines that the shape of at least the waveform portion of the electrical waveform indicates that the fault condition exists.

14. The system of claim 1, wherein the fault condition comprises at least one of:
a full stall of the actuation mechanism;
a partial stall of the actuation mechanism;
a high energy pump stroke;
a low energy pump stroke;
gas accumulation within the medical pump;
air locking of the medical pump;
voltage depletion of a power source;
blockage in a flow path of the medical pump;
an electrical short in the actuation mechanism;
an open switch between the power source and the actuation mechanism; and
an electrical open circuit in the actuation mechanism.

15. The system of claim 1, wherein the processor is configured to determine that the shape of at least the waveform portion of the electrical waveform indicates that the fault condition exists when the processor determines that the shape of at least the waveform portion of the electrical waveform of each of a predetermined number of a set of prior pump strokes indicates that the fault condition exists, or when the processor determines that the shape of at least the waveform portion of the electrical waveform of each of a predetermined number of consecutive pump strokes indicates that the fault condition exists.

16. The system of claim 1, wherein the shape of at least the waveform portion of the electrical waveform applied to the actuation mechanism when the actuation mechanism is energized to provide the pump stroke comprises a shape of at least a waveform portion of an electrical current waveform through the actuation mechanism when the actuation mechanism is energized to provide the pump stroke, and wherein the shape of at least the waveform portion of the electrical current waveform is defined by at least one of:
a time from a start of the electrical current waveform to an initial peak current of the electrical current waveform;
a change in time between the initial peak current and one of a subsequent nadir and a subsequent peak current of the electrical current waveform;
a change in time between a start and an end of the subsequent nadir;
a time from the start of the electrical current waveform to a nadir indicating an end of a pump stroke;
an amplitude value of one or more of the initial peak current, the subsequent nadir, and the subsequent peak current;
a change in current value between the initial peak current and the subsequent nadir;
an initial current rise rate of change of the electrical current waveform; and
a current rate of change of the nadir indicating the end of the pump stroke.

17. The system of claim 1, wherein the sensor comprises at least one of a current sensor and a voltage sensor.

18. The system of claim 1, wherein the processor is configured to initiate an alarm if the processor determines that the shape of at least the waveform portion of the electrical waveform indicates that the fault condition exists.

19. The system of claim 1, wherein the processor is configured to log a time stamp indicating a time at which the fault condition was determined to exist if the processor determines that the shape of at least the waveform portion of the electrical waveform indicates that the fault condition exists.

20. The system of claim 1, wherein the shape of at least the waveform portion of the electrical waveform applied to the actuation mechanism when the actuation mechanism is energized to provide the pump stroke comprises a shape of at least a waveform portion of a voltage waveform across one or more of the actuation mechanism and a capacitor that drives the actuation mechanism when the actuation mechanism is energized to provide the pump stroke, and wherein the shape of at least the waveform portion of the voltage waveform is defined by at least a rate at which a voltage declines over time following a start of the voltage waveform.

21. A medical device system comprising:
a medical pump configured to deliver a therapeutic fluid to a patient, the medical pump comprising an actuation mechanism configured to be energized to provide a pump stroke;
a sensor configured to detect a property associated with energizing the actuation mechanism, the property associated with energizing the actuation mechanism comprising a shape of at least a waveform portion of an electrical waveform applied to the actuation mechanism when the actuation mechanism is energized to provide the pump stroke; and
a processor configured to determine whether the shape of at least the waveform portion of the electrical waveform indicates that a fault condition exists within the medical pump, wherein:
the shape of at least the waveform portion of the electrical waveform applied to the actuation mechanism when the actuation mechanism is energized to provide the pump stroke is a first shape of at least a first waveform portion of a first electrical waveform applied to the actuation mechanism when the actuation mechanism is energized to provide a first pump stroke, and wherein:
the sensor is configured to detect a second shape of at least a second waveform portion of a second electrical waveform applied to the actuation mechanism when the actuation mechanism is energized to provide a second pump stroke subsequent to the first pump stroke, the second shape being different than the first shape, the processor is configured to recognize a progression from the first shape of the at least first waveform portion to the second shape of the at least second waveform portion, and the processor is configured to determine that the fault condition exists within the medical pump by determining that the progression from the first shape of the at least first waveform portion to the second shape of the at least second waveform portion occurs within a predetermined number of pump strokes.

22. The system of claim 21, wherein the processor is further configured to initiate a recovery action to attempt to remedy the fault condition if the processor determines that the shape of at least the waveform portion of the electrical waveform indicates that the fault condition exists.

23. The system of claim 22, wherein the recovery action comprises a recovery sequence initiated by the processor.

24. The system of claim 22, wherein the recovery action comprises at least one of:
delivering a bolus of fluid through the medical pump;
increasing a drive voltage of the actuation mechanism;
increasing or decreasing a charge time of a capacitor that drives the actuation mechanism;
increasing a rate of pump strokes delivered by the medical pump;
initiating a pump reset; and
reinitializing the medical pump.

25. The system of claim 22, wherein the processor is further configured to determine whether the recovery action resolved the fault condition after initiating the recovery action.

26. The system of claim 21, wherein the processor is configured to monitor the medical pump to determine whether the fault condition has been resolved if the processor determines that the shape of at least the waveform portion of the electrical waveform indicates that the fault condition exists.

27. The system of claim 26, wherein the processor is configured to determine that the fault condition has been resolved when the processor determines that the shape of at least the waveform portion of the electrical waveform of each of a predetermined number of a set of prior pump strokes indicates that the fault condition has been resolved, or when the processor determines that the shape of at least the waveform portion of the electrical waveform of each of a predetermined number of consecutive pump strokes indicates that the fault condition has been resolved.

28. The system of claim 26, wherein the processor is configured to log a time stamp indicating a time at which the fault condition was determined to have been resolved if the processor determines that the fault condition has been resolved.

29. The system of claim 26, wherein the processor is configured to initiate an alarm when the processor determines that the shape of at least the waveform portion of the electrical waveform indicates that the fault condition exists and to clear the alarm when if the processor determines that the fault condition has been resolved.

30. The system of claim 21, wherein the actuation mechanism comprises a coil configured to be energized to provide the pump stroke and an actuator that is movable in response to an energization of the coil.

31. The system of claim 21, wherein the fault condition comprises one of a plurality of fault condition types, and wherein the processor is further configured to identify which of the plurality of fault condition types exists if the processor determines that the shape of at least the waveform portion of the electrical waveform indicates that the fault condition exists.

32. The system of claim 21, wherein the fault condition comprises at least one of:
a full stall of the actuation mechanism;
a partial stall of the actuation mechanism;
a high energy pump stroke;
a low energy pump stroke;
gas accumulation within the medical pump;
air locking of the medical pump;
voltage depletion of a power source;
blockage in a flow path of the medical pump;
an electrical short in the actuation mechanism;
an open switch between the power source and the actuation mechanism; and
an electrical open circuit in the actuation mechanism.

33. The system of claim 21, wherein the processor is configured to determine that the shape of at least the waveform portion of the electrical waveform indicates that the fault condition exists when the processor determines that the shape of at least the waveform portion of the electrical waveform of each of a predetermined number of a set of prior pump strokes indicates that the fault condition exists, or when the processor determines that the shape of at least the waveform portion of the electrical waveform of each of a predetermined number of consecutive pump strokes indicates that the fault condition exists.

34. The system of claim 21, wherein the shape of at least the waveform portion of the electrical waveform applied to the actuation mechanism when the actuation mechanism is energized to provide the pump stroke comprises a shape of at least a waveform portion of an electrical current waveform through the actuation mechanism when the actuation mechanism is energized to provide the pump stroke, and wherein the shape of at least the waveform portion of the electrical current waveform is defined by at least one of:
a time from a start of the electrical current waveform to an initial peak current of the electrical current waveform;
a change in time between the initial peak current and one of a subsequent nadir and a subsequent peak current of the electrical current waveform;
a change in time between a start and an end of the subsequent nadir;
a time from the start of the electrical current waveform to a nadir indicating an end of a pump stroke;
an amplitude value of one or more of the initial peak current, the subsequent nadir, and the subsequent peak current;
a change in current value between the initial peak current and the subsequent nadir;
an initial current rise rate of change of the electrical current waveform; and
a current rate of change of the nadir indicating the end of the pump stroke.

35. The system of claim 21, wherein the sensor comprises at least one of a current sensor and a voltage sensor.

36. The system of claim 21, wherein the processor is configured to initiate an alarm if the processor determines that the shape of at least the waveform portion of the electrical waveform indicates that the fault condition exists.

37. The system of claim 21, wherein the processor is configured to log a time stamp indicating a time at which the fault condition was determined to exist if the processor determines that the shape of at least the waveform portion of the electrical waveform indicates that the fault condition exists.

38. The system of claim 21, wherein the shape of at least the waveform portion of the electrical waveform applied to the actuation mechanism when the actuation mechanism is energized to provide the pump stroke comprises a shape of at least a waveform portion of a voltage waveform across one or more of the actuation mechanism and a capacitor that drives the actuation mechanism when the actuation mechanism is energized to provide the pump stroke, and wherein the shape of at least the waveform portion of the voltage waveform is defined by at least a rate at which a voltage declines over time following a start of the voltage waveform.

39. A method of detecting a fault condition within an implantable medical pump, the method comprising:
  delivering, by the medical pump, a therapeutic fluid to a patient, the medical pump comprising an actuation mechanism configured to be energized to provide a pump stroke;
  detecting, by a sensor, a property associated with energizing the actuation mechanism, the property associated with energizing the actuation mechanism comprising a shape of at least a waveform portion of an electrical waveform applied to the actuation mechanism when the actuation mechanism is energized to provide the pump stroke;
  storing, by a processor, a baseline shape that indicates one of a normal pump stroke and a fault condition in a memory;
  comparing, by the processor, the baseline shape to the shape of at least the waveform portion of the electrical waveform applied to the actuation mechanism when the actuation mechanism is energized to provide the pump stroke; and
  determining, by the processor and based on the comparing, whether the shape of at least the waveform portion of the electrical waveform indicates that a fault condition exists within the medical pump.

40. The method of claim 39, further comprising performing a recovery action to attempt to remedy the fault condition if it is determined that the shape of at least the waveform portion of the electrical waveform indicates the fault condition exists.

41. The method of claim 40, wherein performing the recovery action comprises initiating a recovery sequence.

42. The method of claim 40, wherein the recovery action comprises at least one of:
  delivering a bolus of fluid through the medical pump; increasing a drive voltage of the actuation mechanism; increasing or decreasing a charge time of a capacitor that drives actuation mechanism, increasing a rate of pump strokes delivered by the medical pump, initiating a pump reset, reinitializing the medical pump, and placing the medical pump into a reduced delivery mode.

43. The method of claim 40, further comprising determining whether the recovery action resolved the fault condition after performing the recovery action.

44. The method of claim 39, further comprising monitoring the medical pump and determining whether the fault condition has been resolved.

45. The method of claim 44, wherein determining whether the fault condition has been resolved comprises at least one of: determining that the shape of at least the waveform portion of the electrical waveform of each of a predetermined number of a set of prior pump strokes indicates that the fault condition has been resolved, or determining that the shape of at least the waveform portion of the electrical waveform of each of a predetermined number of consecutive pump strokes indicates that the fault condition has been resolved.

46. The method of claim 44, if it is determined that the fault condition has been resolved, further comprising logging a time stamp indicating the time at which the fault condition was resolved.

47. The method of claim 44, further comprising initiating an alarm when it is determined that the shape of at least the waveform portion of the electrical waveform indicates the fault condition exists and clearing the alarm when it is determined that the fault condition has been resolved.

48. The method of claim 39, wherein the fault condition comprises one of a plurality of fault condition types, the method further comprising identifying, by the processor, which of the plurality of fault condition types exists if the processor determines that the shape of at least the waveform portion of the electrical waveform indicates that the fault condition exists.

49. The method of claim 39, wherein the fault condition comprises at least one of: a full stall of the actuation mechanism, a partial stall of the actuation mechanism, a high energy pump stroke, a low energy pump stroke, gas accumulation within the medical pump, air locking of the medical pump, voltage depletion of a power source, blockage in a flow path of the medical pump, an electrical short in the actuation mechanism, and on open switch between a power source and the actuation mechanism.

50. The method of claim 39, wherein determining whether the shape of at least the waveform portion of the electrical waveform indicates that a fault condition exists comprises at least one of: determining whether the shape of at least the waveform portion of the electrical waveform of each of a predetermined number of a set of prior pump strokes indicates that the fault condition exists, or determining whether the shape of at least the waveform portion of the electrical waveform of each of a predetermined number of consecutive pump strokes indicates that the fault condition exists.

51. The method of claim 39, wherein the shape of at least the waveform portion of the electrical waveform comprises a shape of at least a waveform portion of an electrical current waveform through the actuation mechanism when the actuation mechanism is energized to provide a pump stroke, wherein the shape of the current waveform is defined by at least one of: a time from a start of the current waveform to an initial peak current; a change in time between the initial peak current and a subsequent nadir in the current waveform; an amplitude value of the initial peak current; a change in current value between the initial peak current and the subsequent nadir; and a time from the start of the current waveform to a nadir indicating an end of a pump stroke.

52. The method of claim 39, further comprising storing a baseline shape that indicates a normal pump stroke in a memory, and comparing the baseline shape to the shape of the waveform portion of the electrical waveform through the actuation mechanism when the actuation mechanism is energized to provide the pump stroke to determine if the fault condition exists.

53. The method of claim 39, further comprising initiating an alarm if it is determined that the shape of at least the portion of the electrical waveform indicates the fault condition exists.

54. The method of claim 39, further comprising logging a time stamp indicating the time at which the fault condition was determined to exist.

* * * * *